(12) United States Patent
Lentz et al.

(10) Patent No.: US 7,727,736 B2
(45) Date of Patent: Jun. 1, 2010

(54) SOLUBLE PHOSPHOLIPIDS FOR USE IN CLOTTING FACTOR ASSAYS

(75) Inventors: Barry Lentz, Chapel Hill, NC (US); Dougald M. Monroe, III, Carrboro, NC (US); Rinku Majumder, Chapel Hill, NC (US); JinMing Huang, Winston Salem, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 723 days.

(21) Appl. No.: 10/572,521

(22) PCT Filed: Sep. 21, 2004

(86) PCT No.: PCT/US2004/030987

§ 371 (c)(1),
(2), (4) Date: May 22, 2006

(87) PCT Pub. No.: WO2005/031303

PCT Pub. Date: Apr. 7, 2005

(65) Prior Publication Data

US 2007/0037235 A1   Feb. 15, 2007

Related U.S. Application Data

(60) Provisional application No. 60/504,796, filed on Sep. 22, 2003.

(51) Int. Cl.
*C12Q 1/56* (2006.01)
*C12Q 1/00* (2006.01)
*C12P 1/00* (2006.01)
*C12P 21/06* (2006.01)

(52) U.S. Cl. .............................. 435/13; 435/4; 435/41; 435/68.1

(58) Field of Classification Search ........................ None
See application file for complete search history.

(56) References Cited

U.S. PATENT DOCUMENTS

| | | | |
|---|---|---|---|
| 3,486,981 A | 12/1969 | Speck | |
| 4,455,377 A | 6/1984 | Finnerty et al. | |
| 5,443,960 A | 8/1995 | Dahlback | |
| 5,525,478 A | 6/1996 | Matschiner | |
| 5,705,198 A * | 1/1998 | Triplett et al. | 424/542 |
| 6,221,672 B1 | 4/2001 | Baugh et al. | |
| 6,395,501 B1 | 5/2002 | Rosen et al. | |
| 6,438,498 B1 * | 8/2002 | Opalsky et al. | 702/25 |
| 6,451,610 B1 * | 9/2002 | Gorman et al. | 436/69 |
| 6,596,543 B2 | 7/2003 | Wang et al. | |
| 2002/0019021 A1 | 2/2002 | Kraus | |
| 2003/0073070 A1 | 4/2003 | Dai et al. | |
| 2003/0080056 A1 * | 5/2003 | Boos et al. | 210/634 |

FOREIGN PATENT DOCUMENTS

WO    WO 01/44493 A2    6/2001

OTHER PUBLICATIONS

Hürter, P., et al. "Phospholipids of Red Cells and Blood Plasma in Adults, Newborn Infants, and Patients with Rh Erythroblastosis" Pediatrics Aug. 1970 vol. 46 No. 2, pp. 259-266.*
Sigma, "Phosphates" Sigma: Biochemicals and Reagents for Life Science Research, 2000/2001 Catalogue, 2000, pp. 782-791.*
Tans, G., et al. "Meizothrombin Formation during Factor Xa-catalyzed Prothrombin Activation" The Journal of Biological Chemistry. 1991, 266 (32), pp. 21864-21873.*
Banerjee et al., "Role of Procoagulant Lipids in Human Prothrombin Activation. 2. Soluble Phosphatidylserine Upregulates and Directs Factor $X_a$ to Appropriate Peptide Bonds in Prothrombin," *Biochemistry*, 2002, 41, pp. 950-957.
Banerjee et al., "Specificity of Soluble Phospholipid Binding Sites on Human Factor $X_a$," *Biochemistry*, 2002, 41, pp. 7751-7762.
Koppaka et al., "Soluble Phospholipids Enhance Factor $X_a$-Catalyzed Prothrombin Activation in Solution," *Biochemistry*, 1996, 35(23), pp. 7482-7491.
Lentz, "Exposure of platelet membrane phosphatidylserine regulates blood coagulation," *Progress in Lipid Research*, 2003, 42, 423-438.
Lentz, Oral Presentation of "Phosphatidylserine (Not a Membrane Surface) is Required for Efficient Prothrombin Activation" XIX Congress of the International Society on Thrombosis and Haemostatis, Birmingham, United Kingdom, Jul. 12-18, 2003.
Majumder et al., "Effects of Water Soluble Phosphatidylserine on Bovine Factor $X_a$: Functional and Structural Changes Plus Dimerization," *Biophysical Journal*, 2003, 84, pp. 1238-1251.
Majumder et al., "Efficient human thrombin generation requires molecular phosphatidylserine and not a membrane surface," XIX Congress of the International Society on Thrombosis and Haemostatis, Meeting Abstracts, Birmingham, United Kingdom, Jul. 12-18, 2003.
Majumder et al., "Soluble Phosphatidylserine Triggers Assembly in Solution of a Prothrombin-activating Complex in the Absence of a Membrane Surface," *The Journal of Biological Chemistry*, 2002, 277(33), pp. 29765-29773.
Morrissey et al., "Quantitation of Activated Factor VII Levels in Plasma Using a Tissue Factor Mutant Selectively Deficient in Promoting Factor VII Activation," *Blood*, 1993, 81(3), pp. 734-744.
Srivastava et al., "Localization of Phosphatidylserine Binding Sites to Structural Domains of Factor $X_a$," *The Journal of Biological Chemistry*, 2002, 277(3), pp. 1855-1863.
Srivastava et al., "Soluble Phosphatidylserine Binds to a Single Identified Site in the C2 Domain of Human Factor $V_a$," *Biochemistry*, 2001, 40(28), pp. 8246-8255.
Weinreb et al., "Cooperative Roles of Factor $V_a$ and Phosphatidylserine-containing Membranes as Cofactors in Prothrombin Activation," *The Journal of Biological Chemistry*, 2003, 278(8), pp. 5679-5684.

(Continued)

Primary Examiner—Christopher R Tate
Assistant Examiner—Aaron J Kosar
(74) *Attorney, Agent, or Firm*—Myers Bigel Sibley & Sajovec, PA

(57) ABSTRACT

The present invention provides a soluble phospholipid reagent and assays of clotting activity using the same. The methods of the invention can be used to carry out any clotting assay or other assay of clotting activity that traditionally relies on platelet membranes or synthetic membrane preparation by substituting therefor the soluble phospholipids of the invention. Assay compositions and kits comprising the soluble phospholipids of the invention are also provided.

30 Claims, 12 Drawing Sheets

OTHER PUBLICATIONS

Zhai et al., "Phosphatidylserine Binding Alters the Conformation and Specifically Enhances the Cofactor Activity of Bovine Factor $V_a$," *Biochemistry*, 2002, 41, pp. 5675-5684.

Supplementary European Search Report for European Application No. EP04788891.2, Mailed Aug. 6, 2008 (6 Pages).

Gilbert, G. E. et al., "Partial Activation of the Factor VIIIa-Factor IXa Enzyme Complex by Dihexanoic Phosphatidylserine at Submicellar Concentrations", Biochemistry 36(35): 10768-10776, Sep. 2, 1997, XP002489305.

Koppaka, V. et al., "Soluble Phospholipids Enhance Factor Xa-Catalized Prothrombin Activation in Solution", Biochemistry 35(23): 7482-7491, Jun. 11, 1996, XP002489306.

Majumder, R. et al., "Soluble Phosphatidylserine Triggers Assembly in Solution of a Prothrombin-activating Complex in the Absence of a Memebrane Surface", The Journal of Biological Chemistry 277(33): 29765-29773, Aug. 16, 2002, XP002489307.

International Search Report and the Written Opinion of the International Searching Authority for PCT Application No. PCT/US04/30987, mailed Sep. 25, 2007.

Bloor, W.R., "Biochemistry of the Fats," *Chem. Rev.*, 2:243-300 (1925).

Okuda et al., "Usefulnes of synthetic phospholipids in measurement of activated partial thromboplastin time: a new preparation procedure to reduce batch difference," *Clin. Lab. Haem*, 2004, 26: 215-223.

Rosing et al., "The Role of Phospholipids and Factor $V_a$ in the Prothrombinase Complex," *The Journal of Biological Chemistry*, vol. 244, No. 1, Issue of Jan. 10, pp. 274-283, 1980.

Thompson, et al., "A Calorimetric and Fluorescent Probe Study of Phase Transitions in Phosphatidylcholine Liposomes," *Biochemistry of Membrane Transport*, [ed] G. Semenza and E. Cara foli Springer-Verlag Heidelberg 47-71 (1977).

\* cited by examiner

SOLUBLE PHOSPHOLIPIDS FOR USE IN CLOTTING FACTOR ASSAYS

RELATED APPLICATION INFORMATION

This application claims the benefit of U.S. Provisional Application No. 60/504,796, filed Sep. 22, 2003, the disclosure of which is incorporated by reference herein in its entirety.

STATEMENT OF FEDERAL SUPPORT

The present invention was made, in part, with the support of grant numbers HL45916 and 5-P01-HL06350 from the National Institutes of Health. The United States government has certain rights to this invention.

FIELD OF THE INVENTION

The present invention relates to novel reagents and methods for conducting clotting activity assays, in particular, novel soluble phospholipid reagents and clotting activity assays using the same.

BACKGROUND OF THE INVENTION

The traditional "cascade" view of blood coagulation is illustrated in FIG. 1 and consists of two converging pathways: the intrinsic or "contact" pathway was originally defined based on adding clay or other "contact reagents" to blood in a test-tube, and the extrinsic pathway that is now believed to be the pathway by which clotting is initiated following tissue injury. Both of these pathways culminate in the production of blood coagulation factor $X_a$ ($FX_a$, a serine protease) by pathways that depend on membranes. In one of these, factor $IX_a$ ($FIX_a$, also a serine protease) and its cofactor factor $VIII_a$ ($FVIII_a$) activate factor X (FX) in a reaction that is dependent on activated platelet membranes (intrinsic pathway). In the other (extrinsic pathway), FX is activated by another plasma serine protease factor $VII_a$ ($FVII_a$) in conjunction with a cell-membrane located (thus, "extrinsic" to the plasma) cofactor, tissue factor (TF). These two pathways join at the "common pathway," in which $FX_a$ along with its cofactor factor $V_a$ ($FV_a$), activates prothrombin to thrombin in the final step in the blood coagulation cascade. While it is generally believed that the exposure of TF to plasma following tissue damage is the trigger that initiates blood coagulation, it is also clear that the platelet-membrane-dependent complexes ($X_a$-$V_a$, $IX_a$-$VIII_a$) are essential to amplify the process so that a clot will form. Indeed, most of the familial coagulation disorders involve defects in these four proteins.

Prothrombin activation is accomplished by the $FX_a$-$FV_a$ enzyme complex, called "prothrombinase" in the presence of $Ca^{2+}$, and negatively charged membranes (Mann, et al. (1990) *Blood* 76(1):1-16; Rosing, et al. (1980) *J. Biol. Chem.* 255 (1):274-83). In vivo, the membranes derive from activated platelets in the form of vesicles (Sandberg, et al. (1985) *Thromb. Res.* 39(1):63-79; Sims, et al. (1989) *J. Biol. Chem.* 264(29):17049-57) upon whose surface phosphatidylserine (PS) is exposed (Comfurius, et al. (1990) *Biochim. Biophys. Acta* 1026(2):153-60), having been buried on the cytoplasmic surface of resting platelets (Schick, et al. (1976) *J. Clin. Invest.* 57(5):1221-6). PS is known to have a specific role in prothrombin activation (Jones et al. (1985) *Thrombosis Res.* 39, 711-724; Comfurius et al. (1994) *Biochemistry* 33 10319-10324), but the nature of that role has not previously been understood. Because two bonds in prothrombin must be cut, activation can proceed via two possible proteolytic intermediates (FIG. 4), meizothrombin ($MzII_a$), probably the major intermediate in vivo (Rosing and Tans (1988) *Thromb. Haemost.* 60(3):355-60; Nesheim and Mann (1983) *J. Biol. Chem.* 258(9):5386-91) and prethromin 2 plus fragment 1.2 (Pre2 & F1.2; FIG. 2) (Nesheim and Mann (1983) supra; Krishnaswamy, et al. (1987) *J. Biol. Chem.* 262(7):3291-9). Both $FV_a$ and PS-membranes are thought to direct activation through the meizothrombin intermediate, but PS has the major role in this regard (Boskovic, et al. (2001) *J. Biol. Chem.* 276(31):28686-93; Banerjee, et al. (2002) *Biochemistry* 41 (3):950-7; Wu, et al. (2002) *Biochemistry* 41(3):935-49). The fact that PS has this significant role and that it also alters the activity of factor $X_a$ (Koppaka et al. (1996) *Biochemistry* 35:7482) implies a regulatory role for this platelet lipid.

Coagulation factor IX also plays a pivotal role in blood coagulation as shown by the bleeding tendency associated with congenital factor IX deficiency (hemophilia B). The activated form of X, $FIX_a$, plays a key role in thrombin generation at the platelet plug by binding with $FVIII_a$ on platelet membranes to form the Xase complex that activates X to $X_a$. Negatively charged phospholipids, especially PS, are also critical to this process. PS-containing membranes increase the $k_{cat}$ of the factor $VIII_a$-$IX_a$ complex by more than a 1000-fold (Gilbert et al. (1996) *J. Biol. Chem.* 271 11120). $FVIII_a$ and $FIX_a$ bind specifically and with high affinity to PS-containing membranes. However, as for the prothrombinase complex, the exact role of PS in the activation of FX is not known.

Synthetic membrane preparations, which can be derived from phospholipid extracts of platelets, mammalian brain or lung, or soybeans, are commonly used in current clotting assays. More recently, synthetic membranes prepared from mixtures of purified synthetic lipids have been used to improve reproducibility and shelf life of assays. Synthetic phospholipids are also commercially available (e.g., from Avanti® Polar Lipids Inc; Alabaster, Ala.). Even these synthetic membrane preparations suffer from the drawbacks that (1) they are labor-intensive to produce, (2) each batch must be individually calibrated to match clotting times to existing standards (see, e.g., U.S. Pat. No. 6,596,543 B2 to Wang et al.), and (3) they still have only a limited shelf-life.

Accordingly, there is a need in the art for improved reagents and methods for performing clotting assays and other assays of clotting factor activity.

SUMMARY OF THE INVENTION

The present invention is based on the unexpected discovery that soluble phospholipids can be used in place of platelet membranes or synthetic membranes in clotting assays and other clotting activity assays. The inventors demonstrate herein that the prothrombinase complex triggered by soluble phospholipid binding to the human $FX_a$ and $FV_a$ is fully active (i.e., functionally equivalent to the membrane-bound complex) in prothrombin activation.

The soluble phospholipids of the invention have a number of advantages over conventional lipid vesicles in terms of reproducibility, ease of manufacture and improved shelf-life. In addition, the soluble phospholipid compositions disclosed herein may be better suited for use in clotting assays with blood or plasma from lupus patients.

Thus, as one aspect the invention provides for the use of a soluble phospholipid in an assay for clotting activity, wherein the soluble phospholipid is substituted for platelet membranes or synthetic membrane preparations in the clotting factor assay.

As another aspect, the invention provides a method of performing an assay for clotting activity, the improvement comprising substituting a soluble phospholipid for platelet membranes or synthetic membrane preparations in the assay.

As a further aspect, the invention provides a method of evaluating clotting activity comprising:
(a) combining a sample comprising blood or plasma with:
   (i) a soluble phospholipid;
   (ii) a contact activator; and
   (iii) calcium;
(b) incubating the mixture of (a) above for a time and under conditions sufficient for thrombin activation; and
(c) detecting Factor $X_a$ or thrombin activity, wherein the activity of Factor $X_a$ or thrombin is indicative of clotting factor activity in the sample.

As another aspect, the invention provides a method of performing a clotting assay comprising:
(a) combining a sample comprising blood or plasma with:
   (i) a soluble phospholipid;
   (ii) a contact activator; and
   (iii) calcium;
(b) incubating the mixture of (a) above for a time and under conditions sufficient for clot formation.

As yet another aspect, the invention provides a method of detecting a deficiency in intrinsic clotting pathway activity comprising:
(a) combining a sample comprising blood or plasma with:
   (i) a soluble phospholipid;
   (ii) a contact activator; and
   (iii) calcium;
(b) incubating the mixture of (a) above for a time and under conditions sufficient for clot formation;
(c) determining a clotting time for the sample;
(d) comparing the determined clotting time for the sample with a standard, wherein a prolonged clotting time as compared with the standard is indicative of a deficiency in intrinsic clotting pathway activity.

The invention also provides a method of monitoring clotting time in a subject following heparin treatment comprising:
(a) obtaining a sample comprising blood or plasma from a subject that has been given heparin treatment,
(b) combining the sample with:
   (i) a soluble phospholipid;
   (ii) a contact activator; and
   (iii) calcium;
(c) incubating the mixture of (b) above for a time and under conditions sufficient for clot formation;
(d) determining a clotting time for the sample, thereby monitoring clotting time in the subject following heparin treatment.

A still another aspect, the invention provides a method of evaluating Factor $VII_a$ activity comprising:
(a) combining a sample comprising plasma with:
   (i) a soluble phospholipid;
   (ii) soluble tissue factor, and
   (iii) calcium;
(b) incubating the mixture of (a) above for a time and under conditions sufficient for thrombin activation; and
(c) detecting thrombin activity, wherein thrombin activity is indicative of Factor $VII_a$ activity in the sample.

A yet further aspect, the invention provides a method of evaluating the activity of a clotting factor in the intrinsic clotting pathway comprising:
(a) combining a sample comprising plasma with:
   (i) a soluble phospholipid;
   (ii) exogenous Factor X;
   (iii) activated phospholipid-dependent clotting factors other than Factor X that are dependent on the clotting factor being evaluated in the intrinsic clotting pathway or are required for activation of the clotting factor being evaluated; and
   (iii) calcium;
(b) incubating the mixture of (a) above for a time and under conditions sufficient for Factor X activation to Factor $X_a$; and
(c) detecting Factor $X_a$ activity, wherein Factor $X_a$ activity is indicative of the activity of the clotting factor in the sample.

In particular embodiments, this aspect of the invention is practiced to evaluate $FVIII_a$ activity The invention further provides assay compositions and kits for practicing the methods of the invention.

The foregoing and other aspects of the present invention are explained in more detail in the specification set forth below.

DETAILED DESCRIPTION OF THE INVENTION

Figure 7:
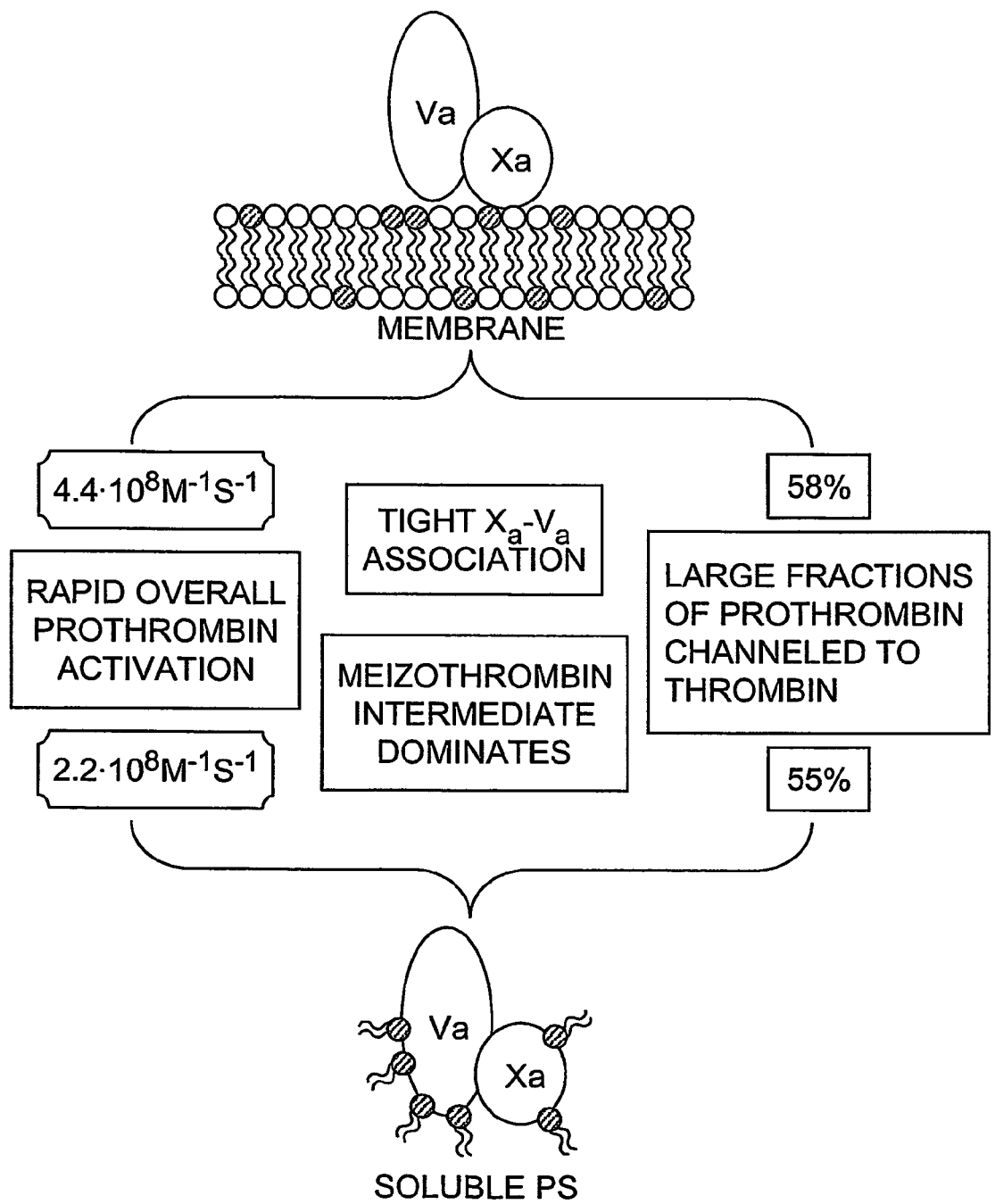
FIG. 7 illustrates that prothrombinase complexes assembled in the presence of either C6PS or of PS/PC membranes are essentially identical. Rates ($k_{cat}/K_M$) of prothrombin activation (left boxes) and percents of prothrombin initially channeled to thrombin (right boxes) are shown for both complexes. Membrane data are well-known (Weinreb, et al. (2003) supra).

The present invention is based, in part, on the unexpected discovery that solubilized phospholipids are functionally equivalent to platelet membranes and can substitute for them in membrane-catalyzed reactions within the intrinsic clotting pathway. In particular, the inventors have shown that a tight prothrombinase complex assembles in solution under the regulatory influence of a solubilized phosphatidylserine (PS). This complex is functionally equivalent to the complex assembled on PS-containing membranes (FIG. 7). The results provided herein further demonstrate that soluble phospholipid molecules regulate the assembly, the activity, and the reaction mechanism of the prothrombinase complex.

The finding that a solubilized phospholipid can replace a phospholipid-containing membrane in the intrinsic clotting cascade and is functionally equivalent thereto is quite surprising. The current understanding of the intrinsic pathway is that a two-dimensional membrane surface is required to bring the individual factors together and to accelerate complex formation. The present inventors have discovered that, in fact, the membrane surface itself is dispensable; phospholipid molecules, whether membrane-bound or in a solubilized form, have specific regulatory and second messenger activity that result in acceleration of the clotting cascade.

The present invention is described below in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Except as otherwise indicated, standard methods can be used for preparing plasma and blood samples, carrying out standard clotting assays or assays for specific clotting factors (e.g., chromogenic or fluorescent assays for thrombin or $FX_a$ activity), clotting factor inhibitors and the like. Such techniques are known to those skilled in the art. See, e.g., Chapters 60 and 69 of Wintrobe's Clinical Hematology, $10^{th}$ edition, G. Richard Lee, John Foerster et al. (eds), Williams & Wilkins, Baltimore (1999); Hemostasis and Thrombosis: Basic Principles and Clinical Practice, $4^{th}$ edition, Robert W. Colman, Jack Hirsh et al. (eds), Lippincott Williams & Wilkins, Philadelphia (2001).

As used in the description of the invention and the appended claims, the singular forms "a," "and" and "the" are intended to include the plural forms as well, unless the context clearly indicates otherwise.

Replacement of Lipid Membranes in Conventional Clotting Assays.

Figure 1:
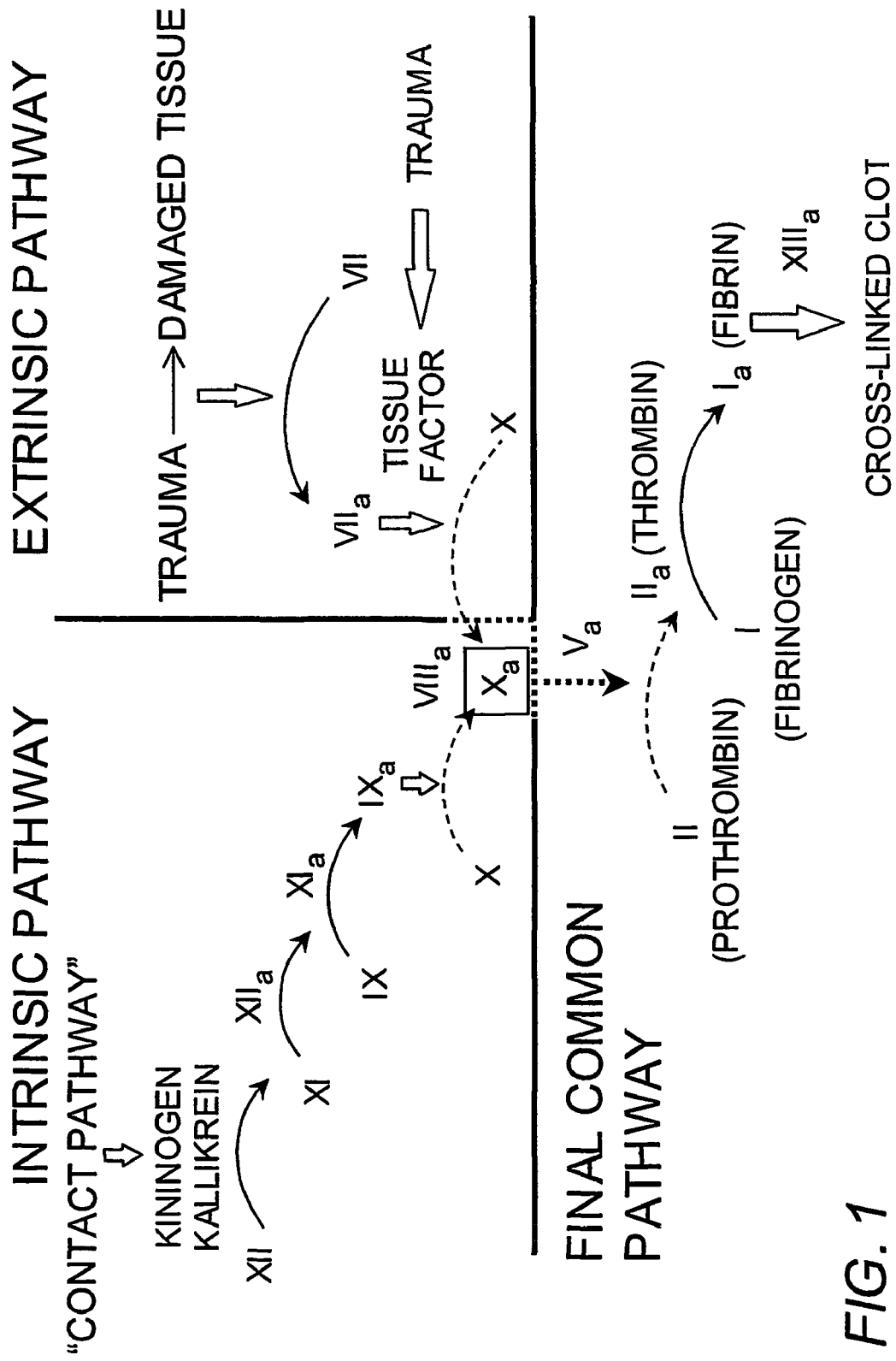
FIG. 1 presents the traditional "cascade" view of blood coagulation. It consists of two converging "pathways", the intrinsic or "contact" pathway that was originally defined based on adding clay or other contact reagent to blood in a test-tube, and the extrinsic pathway that is now believed to be the pathway by which clotting is initiated following tissue injury. These both culminate in the production of factor $X_a$, by reactions that depend on membranes (arrows with a dashed-line), one on activated platelet membranes (intrinsic pathway), and one on membranes of damaged cells at the point of the wound (extrinsic pathway). These two pathways join at the "common pathway", in which prothrombin is activated to thrombin in the final step in the blood coagulation cascade. Thrombin is the central metabolite of blood coagulation. Thrombin production is accomplished by an enzyme complex, called "prothrombinase," that consists of blood coagulation factors $X_a$ ($FX_a$, a serine protease) and $V_a$ ($FV_a$, a cofactor), $Ca^{2+}$, and negatively charged membranes.

As described above, many steps in the clotting cascade are dependent on platelet membranes in vivo (FIG. 1). Conventional assays for evaluating clotting activity or the activity of individual components of the clotting cascade have relied on lipids in the form of synthetic membrane preparations. Such preparations are typically phospholipid extracts (e.g., from mammalian brain or lungs) or synthetic replicates of natural phospholipids, which form insoluble, lamellar membrane-like structures. The present invention can be practiced in connection with any membrane-dependent assay known in the art, where the soluble phospholipids of the invention are substituted for (i.e., used in place of) platelet membranes or synthetic membrane preparations. Alternatively stated, the methods and assay kits of the invention do not rely upon exogenously added platelet membranes or synthetic membrane preparations. "Synthetic membranes" or "synthetic membrane preparation" (and variations thereof) as used herein means any suspension in aqueous buffer of natural or chemically synthesized water-insoluble lipids to form membrane-like surfaces for use in clotting assays. In particular representative embodiments, the present invention is used in connection with assays that measure intrinsic clotting pathway activity or specific assays for $FV_a$ activity, $FVII_a$ activity, $FVIII_a$ activity, $FIX_a$ activity, $FX_a$ activity, or a combination thereof. The soluble phospholipid compositions of the invention can also be used in connection with assays for Activated Protein C (APC) resistance or assays for the presence of other inhibitory (anticoagulant) factors (e.g., antibodies to FV, FVIII, FIX, FX, FXI or prothrombin or lupus anticoagulants).

As used herein, a "soluble" phospholipid comprises essentially no aggregates (e.g., as micelles, lamellar or non-lamellar structures). By "essentially no aggregates," it is intended that the soluble phospholipid contains less than about 5% (weight of lipid as aggregate/total lipid weight) aggregates. Aggregates can be detected and measured by methods known in the art and as described in the Examples below, e.g., by quasi-elastic light scattering (QELS) techniques (see, e.g., Koppaka et al., (1996) *Biochemistry* 35:7482-91). In particular embodiments, a "soluble" phospholipid comprises no detectable aggregates.

In representative embodiments, the soluble phospholipid comprises, consists essentially of, or consists of phosphatidylserine (PS), phosphatidylhomoserine, phosphatidylethanolamine and/or phosphatidic acid. The soluble phospholipid comprises two acylated fatty acid molecules, which can be short, medium or long chain fatty acids, or a mixture thereof. Likewise, the fatty acids can be saturated, monounsaturated, polyunsaturated, or a mixture thereof. In general, phospholipids containing short to medium chain fatty acids are advantageous as they are less likely to form aggregates. Further, as is known in the art, unsaturated fatty acids are less likely to form aggregate structures. Thus, longer unsaturated fatty acids can be employed in the present invention as well. In representative embodiments, the soluble phospholipid comprises acylated C2 to C14 or C16 fatty acids. In other representative embodiments the soluble phospholipid comprises, consists essentially of, or consists of acylated C4 to C10 or C12 fatty acids. In one particular embodiment, the soluble phospholipid comprises, consists essentially of, or consists of C6 phosphatidylserine (i.e., 1,2-dicaproyl-sn-glycero-3-phospho-L-serine; C6PS).

The concentration of the soluble phospholipid used in the inventive assays is not critical as long as the phospholipid remains soluble (as defined above) and is high enough to result in occupancy of the protein regulatory sites for the proteins involved in a particular assay. The soluble phospholipid can be added at any suitable concentration that retains the solubility of the phospholipid and activates the clotting cascade (or portion thereof). In general, the concentration of phospholipid is below the critical micelle concentration, which can be determined using known techniques, such as QELS (see, e.g., Koppaka et al., (1996) *Biochemistry* 35:7482-91). In illustrative embodiments, the soluble phospholipid is added to achieve a final concentration in the reaction mixture of at least about 1 µM, 2 µM, 4 µM, 10 µM, 20 µM, 50 µM or 100 µM and/or less than about 250 µM, 300 µM, 400 µM, 500 µM, 600 µM, 700 µM, 1 mM, 1.5 mM or 2 mM. As described above and understood by those skilled in the art, the particular concentration range that will maintain the phospholipid in a soluble form will vary somewhat based on the type of phospholipid and the length and degree of saturation of the acylated fatty acids, as well as the particular assay conditions, and can be routinely determined by those skilled in the art.

In particular embodiments, the soluble phospholipid is added to the sample as an aqueous solution. As one alternative, the soluble phospholipid is added to the sample as a dried (e.g., lyophilized) composition. This latter approach can be advantageous as the dried composition is easier to handle and transport and has a longer shelf life. Phospholipid compositions can be prepared using known techniques and are available from a variety of commercial sources (e.g., Avanti Polar Lipids Inc; Alabaster, Ala.).

The soluble phospholipids of the invention are "functionally equivalent" to platelet membranes or synthetic membrane preparations in that they can substitute for platelet membranes or synthetic membrane preparations in clotting assays or other clotting activity assays and accelerate phospholipid-activated reactions (e.g., FX→$FX_a$ or prothrombin→thrombin). In particular embodiments, the soluble phospholipids accelerate phospholipid-activated reactions with similar kinetics as membrane preparations. In exemplary embodiments, the rate constant (i.e., $k_{cat}/K_M$) for prothrombin activation by a soluble phospholipid activated prothrombinase complex is on the order of at least about $10^{-7}$, $10^{-8}$ or $10^{-9}$ $M^{-1}s^{-1}$.

One surprising and unexpected advantage of the present invention is that it can be used to carry out assays to evaluate clotting activity on blood or plasma samples from subjects with lupus or samples that otherwise contain lupus anticoagulant factors. Lupus patients have circulating lupus anticoagulants, otherwise known as antiphospholipid antibodies, in their blood and plasma. These antibodies bind to lipid-binding proteins that can associate with synthetic membrane preparations used in conventional assays, thereby interfering with the assay. Paradoxically, the presence of lupus anticoagulants results in a prolonged clotting time because of sequestration of the membrane phospholipids, thereby interfering with membrane-dependent pathways.

Thus, one problem in the art is the lack of suitable assays to evaluate clotting activity in patients with lupus anticoagulants (see, e.g., Blanco et al., (1997) *Thromb Haemost* 77:656-9; Nuss et al., (1999) *Thromb Haemost* 82:1559-60; Ballard et al., (1993) *Br J Rheumatol* 32:515-7; Saxena et al., (1993) *Am J Hematol* 42:232-3; Biron et al., (1996) *Am J Hematol* 51:250-1; Saxena et al., (2000) *Haemophilia* 6:78-83; Triplett et al., (1997) *Am J Hematol* 56: 195-6; Blanco et al., (1998) *Am J Hematol* 58:248). The soluble phospholipids of the present invention do not form aggregate structures recognized by the lupus anticoagulants and, thus, reduce or eliminate interference therefrom.

Clotting Activity Assays.

In one representative embodiment, the invention provides a method of evaluating clotting activity in a blood or plasma sample comprising: (a) combining a sample comprising blood or plasma with a soluble phospholipid, a contact activator and calcium; (b) incubating this mixture for a time and under conditions sufficient for thrombin activation; and (c) detecting a suitable endpoint such as $FX_a$ activity or thrombin activity, wherein the $FX_a$ activity or thrombin activity is indicative of clotting activity in the sample.

In particular embodiments, the methods of the invention comprise providing a blood or plasma sample and combining the sample with the contact activator and incubating this mixture to activate the sample prior to addition of the calcium and soluble phospholipid. The soluble phospholipid and calcium are then added to initiate the clotting cascade.

The terms "evaluate," "evaluates," and "evaluating" (and grammatical equivalents thereof) clotting factor activity or clotting activity are intended broadly and encompass assessment of any impairment (e.g., increases or decreases) in activity, e.g., as compared with activity in a normal sample or subject.

The term "clotting activity" is also used broadly to indicate the ability of the sample to form a clot. The detected endpoint, however, need not be clot formation, although it can be in particular embodiments of the invention. Assays of clotting activity can be clotting assays or, alternatively, can assess the activity of individual clotting factors. Assays for the evaluation of clotting activity also encompass assessments of basal levels of activated clotting factors, the presence of inhibitory factors, resistance to clotting pathway inhibitors, or any other perturbation to the normal clotting pathway.

By "impairment" it is meant any abnormality in clotting activity, which may result from a deficiency or aberrant elevation of clotting factor activity. By a "deficiency" (and grammatical variations thereof) in clotting activity, it is meant that the ability of a sample or subject to form a clot is reduced regardless of the cause, e.g., a decrease in the abundance of circulating clotting factor, impairment in clotting factor activation (e.g., due to lack of activating agents or due to abnormalities in the clotting factor itself), mutations that result in decreased biological activity of the clotting factor, increased turnover of the clotting factor, the presence of inhibitory factors (e.g., antibodies that bind to and neutralize clotting factors such as FV, FVIII, FIX, FX and FXI, Lupus anticoagulants, etc.) and the like. Similarly, an "aberrant elevation" (and grammatical variations thereof) in clotting factor activity can be due to increased levels of circulating clotting factor, reduced clotting factor turnover, increased conversion of the inactive clotting factor to the activated state, mutations that result in enhanced clotting factor activity, reduced level of, or sensitivity to, inhibitory signals, and the like.

Thrombin activity can be determined by any suitable method. For example, chromogenic and fluorescent assays of thrombin enzyme activity are known in the art (see, e.g., Triscott et al., (1999) *Thromb Haemost*, (Suppl):379). Alternatively, and typically more conveniently, thrombin activity can be indirectly assessed by detecting clot formation (discussed in more detail below).

Likewise, methods of assaying $FX_a$ activity are known in the art. Typical assays are based on chromogenic or fluorescent determinations (see, e.g., Rosen et al., (1984) *Scand. J. Haematol*. 33 (Suppl. 40): 139-145). Suitable commercial assays and reagents are available from Chromogenix (Milano, Italy). $FX_a$ activity measurements can also be used as an endpoint to evaluate other clotting factors, e.g., $FVIII_a$ (discussed below).

It is believed that the role of the contact activator in intrinsic clotting pathway assays is to mediate the activation of FXII→$FXII_a$. Any contact activator in the art can be used in connection with the present invention, including particulate and chemical contact activators. Exemplary contact activators include but are not limited to kaolin, clay, silica, celite, diatomaceous earth, glass beads, ellagic acid, or combinations thereof. Ellagic acid based activators comprising phenol and metal ions have been described by U.S. Pat. No. 5,451, 509. The length of time of the contact activation is not critical to the invention and will generally be from about 2 to 5, 7 or 10 minutes.

Calcium is generally added to initiate the clotting activity and is provided in a form that will produce free calcium ions (e.g., calcium chloride or other calcium salt) in the reaction mixture.

In some embodiments of the invention, other divalent metal cations are used instead of, or in addition to, calcium to initiate the clotting activity. Exemplary divalent metal cations include magnesium, manganese, barium, and combinations thereof. As a further alternative, terbium (element 65) or lead can be employed in conjunction with or instead of the divalent metal cations above to initiate clotting activity.

The present invention also encompasses methods of performing clotting assays, in particular, assays to evaluate clotting via the intrinsic clotting pathway. In one representative embodiment, the method comprises: combining a sample comprising blood or plasma with a soluble phospholipid, a contact activator and calcium. The mixture is then incubated for a time and under conditions sufficient for clot formation. In particular embodiments, the reaction mixture is agitated prior to incubation. Those skilled in the art will appreciate that in a sample that has a defect in the clotting pathway, e.g., there is a deficiency in the activity in one of the clotting factors or there is an aberrantly high level in an inhibitory factor, there will be reduced or even no clot formation. Further, clotting factor deficiencies can result in abnormal clot formation, e.g., watery or thin clots. In contrast, in hypercoagulable states, there is an increased propensity for clot formation, which can manifest as abnormally rapid clotting times or high clotting factor activity, even in the presence of inhibitory factors or in the absence of stimuli of the coagulation pathway (e.g., tissue factor).

The standard clinical assay for intrinsic clotting pathway activity is the Activated Partial Thromboplastin Time test (APTT). In general, conventional APTT tests are conducted by incubating a plasma sample pretreated with citrate or other anticoagulant with a particulate or chemical contact activator to activate $FXII \rightarrow FXII_a$ (FIG. 1). Following an activation period (e.g., 2-7 minutes) a synthetic platelet membrane substitute and calcium ions are added to the sample to initiate clotting.

Variations on the APTT assay which use whole blood have been described (see, e.g., U.S. Pat. Nos. 5,039,617 and 5,091, 304; the disclosures of which are incorporated herein by reference for teaching modified whole blood APTT assays).

Another coagulation assay is the Activated Whole Blood Coagulation Time (AWBCT). Typically, the AWBCT is conducted by mixing a whole blood sample with a particulate or chemical contact activator. The sample is then heated and agitated and clotting is monitored.

The normal range of clotting times for particular assays are known, and methods of determining a prolonged or abnormally rapid clotting time would be apparent to those skilled in the art. Normal clotting times are typically on the order of 20-35 seconds; however, it is understood by those skilled in the art that the "normal" clotting time can be shorter or longer with different concentrations of the reagents, such as the soluble phospholipids, and other variations in assay conditions. Methods of standardizing clotting assays are discussed below.

Methods for Identifying Defects the Clotting Pathways.

The methods of the invention are suitable for use in connection with any assay that evaluates the activity of the intrinsic clotting pathway or pathways within the clotting cascade that require phospholipids (traditionally provided in the form of platelet membranes or synthetic membrane compositions). Deficiencies in clotting factors are associated with various forms of hemophilia (e.g., deficiencies in FVIII, FIX and FXI). In contrast, abnormalities that result in an abnormal elevation in clotting activity are associated with increased risk of thrombosis (e.g., deficiencies in antithrombin activity, Protein C activity, Protein S activity or FXII activity, Activated Protein C resistance, the $FV_{Leiden}$ mutation, elevated FVIII activity, thrombomodulin mutants, etc.).

Generally, the first evaluation of clotting factor activity is a clotting assay such as the APTT that will be affected by a wide range of abnormalities. The APTT, however, will only indicate that there in impairment in the clotting pathway. Further assays can be conducted to more specifically identify the defect.

The methods of the invention can be practiced to detect impairments (e.g., deficiencies) in the intrinsic clotting pathway. In one representative embodiment, the invention provides a method of detecting a deficiency in clotting activity comprising: (a) combining a sample comprising blood or plasma with a soluble phospholipid, a contact activator, and calcium; (b) incubating this mixture for a time and under conditions sufficient for clot formation; (c) determining a clotting time for the sample; and (d) comparing the determined clotting time for the sample with a standard, wherein a prolonged clotting time as compared with the standard is indicative of an impairment in intrinsic clotting pathway activity. Alternatively, other endpoints such as thrombin enzyme activity or $FX_a$ activity can be detected.

Once a clotting deficiency has been identified, it is common to follow up with a "mixing test." Typically, the test plasma is mixed 1:1 with normal plasma and the clotting test (or other suitable test of clotting activity) is repeated. If the clotting test provides a normal result, this typically indicates that a clotting factor deficiency is the underlying cause. In contrast, it will generally require further dilution to reverse the effects of an inhibitory factor.

If a clotting factor deficiency is suspected, the methods of the invention can be used to carry out further mixing studies to evaluate and identify the specific clotting factor deficiency. For example, the clotting defective test sample can be combined with reference plasma that has a known deficiency in a particular clotting factor(s). Specific factor-deficient plasmas are commercially available. If the clotting defective test sample can compensate for the known deficiency in the reference plasma, this is an indication that this particular factor is present in the test sample. If combination with the reference plasma does not restore clotting, then the same factor is deficient in the test sample and the reference plasma. In a variation of this approach, purified clotting factors can be added to the test sample prior to the clotting assay. To illustrate, FVIII can be added to a clotting defective test sample. If addition of the exogenous factor restores normal clotting activity, then it can be presumed that the test sample has a deficiency in FVIII activity. These methods can be practiced to identify a deficiency in the activity of any of the clotting factors involved in the intrinsic pathway, e.g., FI (i.e., fibrin), FII (i.e., thrombin), FV, FVIII, FIX, FX, FXI, FXII. In particular, the invention is useful for screening for $FVIII_a$, $FIX_a$ and $FXI_a$ deficiencies, which are the most common deficiencies and are associated with hemophilias A, B and C, respectively.

The level of clotting factor activity in the test sample can further be determined by comparison with a standard curve generated by preparing a range of dilutions of normal plasma with factor-deficient plasma and determining a clotting time for each. The clotting time of the sample can then be compared with the standard curve to determine what % of clotting factor is present in the test sample as compared with normal plasma.

The present invention also encompasses methods of evaluating the activity of a clotting factor in the intrinsic clotting pathway (FV, FVIII, FIX or FX), including phospholipid-dependent clotting factors (e.g., a clotting factor that requires platelet membranes or synthetic membranes for activation or activity). For example, one current assay is a $FVIII_a$ chromogenic assay that is used to specifically identify $FVIII_a$ deficiency, which is associated with hemophilia A. Commercial assays based on chromogenic detection of $FVIII_a$ are available from Chromogenix (Milano, Italy), such as the COATEST® VIII:C/4 test. According to the present invention, exogenous $FIX_a$, exogenous FX and soluble phospholipids are combined with a plasma sample. In the presence of $FVIII_a$ in the plasma sample, FX will be activated to $FX_a$. $FX_a$ activity can be detected using known techniques (see, e.g., Rosen et al., (1984) *Scand. J. Haematol.* 33 (Suppl. 40): 139-145). Alternatively, thrombin enzymatic activity or clot formation can be detected. In a variation of the Chromogenix assay, small amounts of thrombin can be added to the system to activate $FVIII \rightarrow FVIII_a$.

Similar assays can be used to evaluate the activity of other phospholipid-dependent clotting factors. For example, $FVIII_a$ (or FVIII and a FVIII activator), rather than $FIX_a$, can be added to the system described above to assess $FIX_a$ activity in the sample. To evaluate $FX_a$ activity in the plasma sample, $FVIII_a$ (or FVIII and a $FVIII_a$ activator) and $FIX_a$ can be added to the plasma and $FX_a$ or thrombin activity (e.g., by detecting thrombin enzymatic activity or clot formation) assessed. This assay system depends on the plasma to provide the clotting factor being evaluated to initiate the clotting cascade. If there is an impairment in clotting (or whatever other endpoint is being detected), it can be inferred that the sample was deficient for the particular factor being assessed as all other necessary component are provided to the assay system. In other words, all factors, other than the factor being evaluated, which would be required for clotting pathway activity are provided. Thus, if there is an impairment in clotting factor activity it can be attributed to a deficiency in the factor being evaluated as all other necessary factors are provided.

Thus, the invention provides methods of evaluating the activity of a clotting factor in the intrinsic clotting pathway comprising: (a) combining a sample comprising plasma with: a soluble phospholipid, exogenous Factor X and activated forms of clotting factors other than FX that are dependent on the clotting factor being evaluated in the intrinsic clotting pathway or are required for activation of the clotting factor being evaluated, and calcium; (b) incubating this mixture for a time and under conditions sufficient for Factor X activation to Factor $X_a$; and (c) detecting Factor $X_a$ activity, wherein Factor $X_a$ activity is indicative of the activity of the clotting factor in the sample. $FX_a$ activity can be directly assessed (e.g., by a chromogenic or fluorescent assay) or can be indirectly assessed by detecting thrombin enzymatic activity or clot formation.

The invention can also be used in methods of detecting and/or identifying inhibitory factors. Inhibitory factors include clotting factor inhibitors (i.e., antibodies that neutralize the clotting factors), heparin and lupus anticoagulants.

The methods of the invention can be used to identify, and optionally quantify, autoantibodies (sometimes called inhibitors) of clotting factors (e.g., autoantibodies to FV, FVIII, FIX, FX or FXI). The titer of these inhibitors in the sample or subject is called a "Bethesda titer" (Ewing & Kasper, (1982) *Am J. Clin. Pathol.* 77:749-52). Low Bethesda titers can be treated by administering excess amounts of the clotting factor against which the autoantibody is directed to overcome the inhibitory effects. High Bethesda titers cannot generally be treated with this approach. Assays to determine Bethesda titers are based on mixing tests that involve determining how much a test plasma containing inhibitors has to be diluted into normal plasma to reduce the clotting time to normal. In one standard assay, various dilutions of test plasma with normal plasma are incubated at 37° C. for 2 hours. The inhibitor titer is the reciprocal of the dilution of test plasma containing inhibitor that neutralizes 50% of normal clotting factor activity. These assays can further be used to monitor clotting factor replacement therapy to determine whether patients are receiving sufficient clotting factor.

With respect to lupus anticoagulants, the invention can be used in methods of identifying the presence of lupus anticoagulants as opposed to other inhibitory factors. For example, a clotting or $FX_a$ assay can be carried out in the presence of soluble phospholipids and conventional synthetic membrane preparations. A prolonged clotting time or low $FX_a$ activity in the presence of synthetic membranes with a normal clotting time or $FX_a$ activity with the soluble phospholipids indicates the presence of lupus anticoagulants in the sample.

APC Resistance Assays.

The methods of the invention can also be used to evaluate abnormal elevations in clotting activity (i.e., hypercoagulable states).

To illustrate, as yet another application, the soluble phospholipids of the present invention can be used in connection with Activated Protein C (APC) assays, which assess resistance to the anti-coagulatory effects of Protein C. Protein C prevents uncontrolled coagulation and migration of the activated blood clotting factors from the site of vascular injury. Thrombin escaping from the site of hemostasis will bind to thrombomodulin, a cell bound receptor, which reduces the procoagulant activity of thrombin (i.e., ability to convert fibrinogen→fibrin). This interaction between thrombin and thrombomodulin also modulates thrombin activity to turn it into a specific activator of the zymogen Protein C. Activated Protein C (APC) is a serine protease that, in the presence of Protein S, inactivates $FV_a$ and $FVIII_a$, thereby markedly slowing the coagulation cascade.

Some individuals have impairments in the ability of APC to inactivate $FV_a$ and are termed "APC resistant." Such subjects are at increased risk for thrombosis. APC resistance can result from hereditary or acquired deficiencies in normal Protein C or Protein S activity. The most prevalent form of APC resistance is a result of a specific mutation in FV (mutation of $Arg^{506} \rightarrow Gln^{506}$) that produces an APC resistant form of FV termed "$FV_{Leiden}$."

Addition of APC to plasma or blood from normal subjects results in a slowing down of the coagulation process and a prolonged clotting time (alternative results include reduced thrombin enzymatic activity or reduced $FX_a$ activity, etc.). APC resistance is manifested as an impairment in this inhibitory pathway, with continued rapid clotting (or alternatively, high thrombin enzymatic activity, high $FX_a$ activity, etc.).

APC resistance assays are known in the art, and include assays described in international patent publications WO 93/10261 and WO 96/04560, U.S. Pat. No. 6,426,192 and Dahlback et al., (1993) *Proc. Nat. Acad. Sci.* 90:1004-08 (incorporated by reference herein in their entireties). Suitable commercial assay kits and reagents are also available from Chromogenix (Milano, Italy), such as the COATEST® APC™ Resistance assay. The existing assays, which rely on synthetic membrane preparations, are relatively unreliable. For example, these assays are not sufficiently sensitive and reproducible to accurately identify $FV_{Leiden}$ heterozygous individuals, who typically exhibit less APC resistance than homozygous individuals. Use of soluble phospholipid in place of the synthetic membrane preparations may increase the reproducibility of the assay and permit better discrimination between heterozygous and normal individuals.

In one representative embodiment of the present invention, the APC resistance assay comprises: (a) combining a sample comprising blood or plasma with a soluble phospholipid, a contact activator, calcium and APC or a Protein C activator; (b) incubating this mixture for a time and under conditions sufficient for thrombin activation; and (c) detecting thrombin activity, wherein thrombin activity is indicative of APC resistance. Thrombin activity can be measured directly or by clot formation. In particular embodiments, the contact activator and phospholipids are added first, and following contact activation, the APC or Protein C activator and calcium are added to initiate the coagulation cascade. Further, many existing assays dilute the test plasma with FV deficient plasma prior to the assay (e.g., one part test plasma: 4 to 20 parts FV deficient plasma), thereby increasing the sensitivity of the assay to $FV_a$ concentrations. Such modifications can also be combined with the methods of the invention.

Any endpoint that indicates the level of $FV_a$ known in the art can be used in the APC resistance assay, including but not limited to direct measurement of $FV_a$ activity, $FX_a$ activity, thrombin enzymatic activity and detection of clot formation. Recently, a chromogenic APC assay has been described in which $FX_a$ is added to diluted plasma in the presence of calcium, phospholipids and APC or a protein C activator. The measured end-point is hydrolysis of a chromogenic substrate by thrombin. APC resistance will impede the rate of $FV_a$ inactivation by APC and will result in higher levels of thrombin generation as compared with normal plasma.

APC resistance can be determined by comparison with a standard such as normal plasma or values based on historical clinical information (as described below). The most common approach, however, is to determine a ratio of clotting time (or another suitable end-point such as thrombin activity or $FX_a$ activity) in the presence and absence of APC. Typical APC clotting ratios (clotting time with APC/clotting time without APC) for healthy subjects are in the range of about 2-5, and are less than about 2 for APC resistant individuals (e.g., values of about 1.4-1.8 for heterozygous $FV_{Leiden}$ and about 1.1-1.3 for homozygous $FV_{Leiden}$). One commercial assay (Chromogenix COATEST® APC™ assay recommends an APC resistance cut-off value as 0.75 to 0.80 times the median APC ratio for normal plasma.

Thrombin in the presence of thrombomodulin is one activator of Protein C. Other activators of Protein C are known in the art and include snake venom extracts and purified fractions from snake venom. Illustrative snake venoms containing Protein C activators include venoms from *Agkistrodon contortrix contortrix* or from species of Elapidae such as *Notechis, Tropidechis, Crptophys, Hoplocephalus* and *Pseudechis* (e.g., *Notechis scutatus scutatus, Notechis ater niger, Notechis ater humphreysi, Notechis ater serventyi, Notechis finders, Notechis occidentalis, Tropidechis carinatus, Cryptophis nigrescens, Hoplocephalus stephensii* and *Pseudechis porphyriacus*). The activating factors from the snake venom can also be produced using recombinant nucleic acid techniques, e.g., from microorganisms, insect cell cultures, mammalian cell cultures and the like.

PROTAC® (American Diagnostica, Greenwich, Conn.) is a serine protease and Protein C activator that is isolated and purified from the venom of the southern copperhead snake (*Agkistrodon contortrix contortrix*).

Another cause of APC resistance is a deficiency in Protein S activity (e.g., due to reductions in the abundance of Protein S, the biological activity of the protein, or the presence of inhibitors). Protein S is the cofactor of APC. While there is some disagreement in the literature about how much rate enhancement Protein S contributes to the proteolytic activity of APC, it is clear that its rate-enhancing effects require PS-containing membranes (Norstrom et al., (2003) *J. Biol. Chem.* 278:24904). Commercial kits for detecting Protein S activity are available from American Diagnostica (Greenwich, Conn.). In one representative Protein S assay that can be modified for use with the soluble phospholipids of the invention, test plasma is diluted with Protein S depleted plasma. A reagent containing $FX_a$, APC and soluble phospholipid is then combined with the mixed plasma and calcium is added to initiate clot formation. Normal plasma, but not plasma with a Protein S deficiency, will correct the APC resistance in the Protein S depleted plasma. Prolongation of clotting time is directly proportional to the concentration of Protein S in the test plasma, which can be compared with a standard curve. As an alternative, Protein S assays can be carried out as a variation of the APC assays described above, with the exception that the test plasma is diluted with Protein S depleted plasma.

Elevated Factor $VII_a$ Levels.

Another recognized impairment in clotting activity is a result of abnormal elevations in basal $FVII_a$ levels. As another example of how the present invention can be used in evaluating clotting activity, SPS can be substituted for PS-containing membranes in assays for Factor $VII_a$ activity. FVII is converted to $FVII_a$ in the presence of tissue factor (TF), which also acts as a potent cofactor of $FVII_a$ activity. In particular, $FVII_a$ in the presence of TF activates $FX \rightarrow FX_a$. Some individuals have a higher basal level of $FVII_a$ (i.e., in the absence of TF or tissue damage) and appear to be at greater risk for thrombosis. TF is generally embedded within membranes and it is believed that membrane-associated TF is required for FVII activation to $FVII_a$ but not as a cofactor of $FVII_a$ in FX activation (i.e., a soluble TF can act as a $FVII_a$ cofactor).

Methods of detecting and, optionally, quantifying $FVII_a$ levels are known in the art (see, e.g., Morrissey et al., (1993) *Blood* 81:734; Kapur et al., (1996) *Arteriosclerosis, Thrombosis*, and *Vascular Biology* 16:1327-32), and can be modified to incorporate the soluble phospholipids of the present invention in place of synthetic membrane preparations.

A representative method of evaluating $FVII_a$ activity according to the invention comprises: (a) combining a sample comprising plasma with a soluble phospholipid, soluble tissue factor and calcium; (b) incubating this mixture for a time and under conditions sufficient for $FX_a$ or thrombin activation; and (c) detecting $FX_a$ activity or thrombin activity (e.g., by enzymatic assay or clot formation), wherein $FX_a$ activity or thrombin activity is indicative of Factor $VII_a$ activity in the sample. While not wishing to be held to any theory of the invention, in the presence of soluble TF, FVII will not be activated to $FVII_a$. Thus, the assay evaluates basal levels of $FVII_a$. The soluble TF accelerates $FVII_a$ activation of FX in the presence of soluble phospholipid. Any suitable endpoint can be detected, e.g., $FX_a$ activity, thrombin enzyme activity or clot formation. In the presence of elevated $FVII_a$ levels as compared with normal plasma, there will be increased $FX_a$ activity, increased thrombin enzyme activity or a more rapid clotting time as compared with normal plasma.

Soluble (e.g., not membrane-associated) tissue factor can be prepared by any method known in the art. For example, TF can be solubilized by treating membranes containing TF with a detergent. In this case, SPS would be expected to associate with the detergent micelles. Alternatively, the TF can be truncated so that the membrane-associated portion is removed (see, e.g., Morrissey et al., (1993) *Blood* 81:734; U.S. Pat. Nos. 5,750,358; 5,741,658).

Monitoring Subjects Prior to Surgery and/or Following Anti-Coagulation Therapy.

The inventive methods can also be used to evaluate clotting activity in a subject prior to surgery. Alternatively, the methods can be practiced to monitor clotting time following anti-coagulation therapy (e.g., heparin therapy prior to or during surgery). In one representative embodiment, the method comprises: (a) obtaining a sample comprising blood or plasma from a subject that has been given anticoagulation therapy (e.g., heparin); (b) combining the sample with a soluble phospholipid, a contact activator, and calcium; (c) incubating this mixture for a time and under conditions sufficient for clot formation; (d) determining a clotting time for the sample, thereby monitoring clotting time in the subject following heparin treatment. Alternatively, other endpoints such as thrombin enzyme activity or $FX_a$ activity can be monitored.

The assay can be performed one or more additional times to monitor the subject over time. For example, samples can be taken from the subject at timed intervals (e.g., over minutes, hours or even days) to follow or monitor the effects of the anticoagulant therapy over time.

Prior art methods of evaluating intrinsic pathway clotting activity rely on platelet membranes or, more commonly, synthetic membrane substitutes. In contrast, the present invention uses soluble phospholipids in place of the platelet membranes or synthetic membrane preparations. Conventional membrane-based clotting assays have suffered from a number of drawbacks, including high background, variability, difficulty in producing high quality and reproducible batches of the synthetic membranes, and the relatively short shelf life (i.e., instability) of these preparations.

In contrast, assays incorporating the soluble phospholipid compositions of the invention may have a lower background and be more reproducible. Moreover, the soluble phospholipid compositions are easier and less expensive to prepare, with reduced batch to batch variability, and have a longer shelf life under room temperature, refrigerated or freezer conditions. In particular embodiments, the soluble phospholipid in dried form has a shelf life of at least about 4, 6, 8, 10, 12 or 18 months or longer at refrigerated (e.g., around −4° C.) or freezer (e.g., −20° C.) conditions. In other embodiments, stability of the dried soluble phospholipid at room temperature is at least about 2, 3, 4, 5, 6 or 9 months or longer. Dried phospholipids can be readily solubilized, e.g., in water or other aqueous solution, and store extremely well when stored as a dried powder.

Samples and Assay Conditions.

Any suitable sample can be used to carry out the methods of the invention, typically a blood or platelet poor plasma (PPP) sample, depending on the particular assay being used. In representative embodiments, the sample is mixed with an anti-coagulant (e.g., a citrate salt such as sodium citrate) to prevent clotting prior to initiation of the assay. The sample can be derived from any mammalian or avian subject. Suitable mammalian subjects include humans, non-human primates, cats, dogs, horses, rabbits, rats, mice, hamsters, guinea pigs, sheep, goats, cattle and pigs. Suitable avian subjects include chickens, turkeys, quail, ducks, geese, parrots and parakeets.

As indicated above, numerous assays are known in the art to evaluate intrinsic clotting pathway activity. These assays can be modified to incorporate the soluble phospholipids of the invention in place of platelet membranes or synthetic membrane preparations. Thus, suitable reaction conditions (e.g., time and temperature) for clotting activity assays are well known in the art. Typically, the assays are carried out at room temperature or physiological temperature (e.g., 37° C.).

As discussed above, the inventive methods can be practiced to perform a clotting assay. In representative embodiments of this aspect of the invention, a clotting time is determined for the sample, e.g., the amount of time for a solid clot to form. Alternatively, or additionally, the method is carried out to provide a qualitative evaluation of the clot. Normal samples produce a strong gel clot. Samples that yield thin, watery or webby clots or with prolonged clotting times are indicative of a clotting abnormality.

Detection of Clot Formation.

A variety of techniques and detection devices are known for detecting clot formation. Generally, most of these protocols and devices rely on detection of the increase in turbidity or viscosity in the sample. Visual inspection with the human eye (with or without a microscope or other magnifying instrument) can also be used to detect clot formation. Automated instruments typically monitor optical properties, mechanical properties or electrical conductivity. For example, one traditional approach employs an instrument that measures increasing conductivity during clot formation. Fibrometers are instruments that mechanically detect clot formation as an increase in sample viscosity. Likewise, turbidity can be optically detected by the decrease in light transmission through the sample due to clot formation.

More advanced instruments, such as the KoaguLab® (Ortho Diagnostic systems Inc., Raritan, N.J.), generate a printed graph plotting turbidity against reaction time. The shape of the curve provides a "clot signature," which can be evaluated by clinicians. The HEMOCHRON® (International Technidyne Corp., Edison, N.J.; see, e.g., U.S. Pat. Nos. 3,836,333 and 3,695,842) or the Sigma Amelung AMAX CS-190® coagulation analyzer can also be used to determine clotting time. Other instruments for detecting coagulation and measuring clotting times are known in the art.

Devices and methods are also known in the art that calculate the rate or velocity of clot formation (see, e.g., U.S. Pat. No. 5,169,786).

Standardized Methods.

In some embodiments of the invention, impaired clotting activity is determined by comparison with a standard. For example, based on historical experience with the assay, a threshold value can be selected as a reference value for comparison with the clotting activity in the test sample. For example, a clotting time in the test sample that is greater than the reference value or is greater than the reference value by a specified amount (e.g., at least about 5%, 7%, 10%, 15%, 20%, 25%, 30%, 40% or 50% greater or even two-fold or three-fold greater or more) presumptively identifies the sample as having a deficiency in clotting activity. Alternatively, reductions in the activity of individual clotting factors of at least about 5%, 10%, 15%, 20%, 25%, 33%, 40%, 50%, 60%, 75%, 80%, 90% or more can be used to identify a test sample as having a deficiency in clotting activity. Statistical analysis can also be used to identify assay values times that are significantly greater or less than the reference value. Typically, the reference value will be based on known assay values in samples from healthy subjects.

One system for normalizing clotting times is the International Normalized Ratio (INR). Normal plasma will give an INR value of 1. Values greater than a particular ratio presumptively identifies a subject as having a deficiency in clotting activity. For example, an INR value of more than about 1.05, 1.07, 1.1, 1.15, 1.2, 1.25, 1.33, 1.4, 1.5, 1.75, 2.0 or 3 or greater can be used to identify subjects with clotting deficiencies.

The choice of reference value can be based on a number of factors including past clinical experience, the reproducibility of the assays, tolerance of false negative or false positive results, cost-benefit of early diagnosis, and the like.

Likewise, a standard can be used to determine abnormally rapid clotting times or abnormally elevated clotting factor activity.

In some approaches, the reference value is determined concurrently using a sample(s) from a normal subject(s) or a synthetic composition that is known to provide assay values that are similar to those from normal blood or plasma as a standard. By "concurrently" it is not necessary that the samples be analyzed at the same time. "Concurrently" indicates that the standard and the test sample are analyzed sufficiently close in time such that a meaningful comparison can be made between the sample and the standard.

Recommended standards for identifying samples with impaired clotting activity are typically provided by the manufacturer of commercial assays and devices.

Kits and Assay Compositions.

As further aspects, the present invention provides assay compositions (e.g., reagent mixtures) and kits for carrying out the methods of the invention. In representative embodiments, an assay composition according to the invention comprises: (a) a plasma sample; (b) a soluble phospholipid; (c) an additional reagent such as a contact activator, a soluble tissue factor, and/or exogenous Factor X; and (d) calcium. In particular embodiments, the assay composition does not contain exogenously added platelet membranes or synthetic membranes. In other particular embodiments, the assay composition above comprises a contact activator and further comprises Activated Protein C or a Protein C activator. In still other embodiments, the assay composition above comprises exogenous Factor X and exogenous Factor $IX_a$. The assay composition can further comprise a clotting factor deficient plasma or a Protein C or Protein S deficient plasma.

An exemplary kit for practicing the methods of the invention comprises: a soluble phospholipid, an additional reagent such as a contact activator, a soluble tissue factor and/or a composition comprising Factor X. The kit can further comprise a calcium reagent, exogenous clotting factors in the inactive or activated form, clotting factor deficient plasma, Protein S or Protein C depleted plasma, and/or a suitable standard. In one representative embodiment, the kit above comprises a contact activator and further comprises Activated Protein C or a Protein C activator. In other embodiments, the kit above comprises a composition comprising Factor X and a composition comprising Factor $IX_a$, which may be provided as separate or as a single reagent.

The kit can further comprise other reagents such as enzymes, salts, buffers, detergents and the like for carrying out the inventive methods. The components of the kit are packaged together in a common container, typically including instructions for performing selected specific embodiments of the methods disclosed herein.

EXAMPLES

The Examples, which follow, are set forth to illustrate the present invention, and are not to be construed as limiting thereof. In the examples, DAPA means dansylarginine-N-(3-ethyl-1,5-pentanediyl) amide; SDS-PAGE means sodium dodecyl sulfate polyacrylamide gel electrophoresis; S-2238 means H-D-phenylalanyl-L-pipecolyl-L-arginin-p-nitroanilid dihydrochlorid; S-2765 means N-α-benzyloxycarbonyl-D-arginyl-L-glycyl-L-arginin-p-nitroanilid dihydrochlorid; DOPC means 1,2-dioleoyl-3-sn-phosphatidylcholine; C6PS means 1,2-dicaproyl-sn-glycero-3-phospho-L-serine; Pre2 means prethrombin 2; $II_a$ means thrombin; $MzII_a$ means meizothrombin; and F1.2 means fragment 1.2.

Two key reactions of blood coagulation, factor X and prothrombin activation, require membranes. In vivo, these membranes are small vesicles released from activated platelets containing a negatively charged lipid, phosphatidylserine (PS) (Bode et al. (1985) *Thrombosis Res.* 39 49; Jones et al. (1985) *Thrombosis Res.* 39 711; Sims et al. (1988) *J. Biol. Chem.* 263:18205). These two reactions involve highly homologous enzymes and cofactors, namely factors $IX_a$ and $VIII_a$ in factor X activation, and $X_a$ and $V_a$ in prothrombin activation. In Example 1, we show that a fully active human prothrombin-activating complex, prothrombinase, can be assembled in solution using SPS and does not require a surface of any kind. It is established that negatively charged phospholipids, especially PS, play a prominent role in controlling the factor X-activating complex (Xase) complex (Gilbert et al. (1996) *J. Biol. Chem.* 271 11120). In Example 2, we present preliminary results suggesting that SPS will be able to play the same role in promoting formation of a human Xase. Finally, in Example 3, we show that SPS plays the same role as PS-containing membranes in the down-regulation of thrombin generation by APC.

Example 1

C6PS Assembly and Regulation of Prothrombin-Generating Complex

Materials and Methods

Materials. Ecarin from *Echis carinatus* snake venom, heparin, and EGTA were purchased from SIGMA Chemical Company (St. Louis, Mo.). Dansylarginine-N-(3-ethyl-1,5-pentanediyl) amide (DAPA) was obtained from Hematologic Technologies Inc. (Essex Junction, Vt.). Thrombin-specific substrate, S-2238, and the factor $X_a$ substrate, S-2765, were purchased from AB Kabi Diagnostica (Molndal, Sweden). 1,2-dicaproyl-sn-glycero-3-phospho-L-serine (C6PS) was purchased from AVANTI® Polar Lipids Inc. (Alabaster, Ala.), and stock solutions were prepared from the purchased chloroform stock using well-known methods (Banerjee, et al. (2002) *Biochemistry* 41(3):950-7). Human prothrombin and factor $X_a$ and Pre2 and F1.2 were obtained from Hematologic Technologies Inc. (Essex Junction, Vt.), and $MzII_a$ was prepared as described (Pei and Lentz (1991) *Blood Coagul. Fibrinolysis* 2(2):309-16). DEGR-$X_a$ was prepared as described (Majumder, et al. (2002) supra). Purified human factor V was prepared from fresh frozen human plasma (American Red Cross Center, Durham, N.C.) and then activated to factor $V_a$ according to standard methods (Kane and Majerus (1981) *J. Biol. Chem.* 256(2):1002-7; Cutsforth, et al. (1996) *Biophys. J.* 70(6):293849). The activity of $FV_a$ was assayed using 25/75 PS/PC vesicles according to well-established methods (Krishnaswamy, et al. (1989) *J. Biol. Chem.* 264(6):3160-8).

Critical Micelle Concentration (CMC) Determination. Controls to check for the occurrence of C6PS micelles were performed by measuring the diameters of aggregates using quasi-elastic light scattering (Koppaka, et al. (1996) *Biochemistry* 35(23):7482-91). This method is capable of detecting both the minimal micelles formed by pure C6PS as well as the larger aggregates formed in the presence of prothrombin, $FX_a$, $FV_a$, or a combination of these proteins (Koppaka, et al. (1997) *Biophys. J.* 73(5):2638-52; Zhai, et al. (2002) supra; Majumder, et al. (2002) supra). CMCs determined by this method agree with values determined by changes in factor $X_a$ activity (Koppaka, et al. (1997) supra), in the fluorescence of surface-seeking fluorescence probes (Koppaka, et al. (1997) supra), and in CD spectra of factor $X_a$ (Majumder, et al. (2003) supra).

Preparation of Phospholipid Vesicles. Extruded large unilamellar vesicles (LUV) composed of 25/75 bovine PS and DOPC were prepared, and phospholipid concentration was determined by previously described methods (Wu, et al. (2002) supra).

Fluorescence Stopped-Flow Measurements. The rates of thrombin formation from either MzII$_a$ or Pre2 (with equimolar fragment 1.2), or of thrombin plus MzII$_a$ formation from human prothrombin, were estimated from the time-dependent fluorescence change of DAPA bound to the activation products. The use of DAPA for this purpose is well-established (Nesheim, et al. (1979) *Biochemistry* 18(6):996-1003; Nesheim, et al. (1979) *J. Biol. Chem.* 254(21):10952-62; Krishnaswamy, et al. (1987) supra), and prothrombin activation rates measured in the presence of PS/PC membranes by this method were shown to be equivalent to rates measured either with thrombin-specific substrates or with quantitative SDS-PAGE (Wu, et al. (2002) supra; Weinreb, et al. (2003) *J. Biol. Chem.* 278(8):5679-5684). Stopped-flow measurements were performed using an SLM-Aminco Milliflow® stopped flow reactor (Spectronic Instruments, Inc., Rochester, N.Y.) attached to the SLM 48000® spectrofluorometer (Spectronic Instruments) as described (Wu, et al. (2002) supra; Weinreb, et al. (2003) supra). Syringe A contained substrate solution and DAPA in 50 mM Tris, 150 mM NaCl, 5 mM CaCl$_2$, pH 7.5, and syringe B contained pre-assembled prothrombinase (FX$_a$, FV$_a$ and C6PS) in the same buffer, with the final concentrations of factors X$_a$ and V$_{a2}$ in the reaction chamber being 1 and 5 nM and the substrate/DAPA ratio being 1/5. The calculation of rates from measurements of initial fluorescence intensity (F$_0$) and intensity at the completion of the reaction (F$_\infty$) is well-established (Nesheim and Mann (1983) supra; Wu, et al. (2002) supra).

Rapid Chemical Quench Measurements. Rapid quench experiments, using the Chemical-Quench-Flow Model RQF-3 from Kintek Corporation (State College, Pa.), were performed at 37° C. as described (Wu, et al. (2002) supra; Weinreb, et al. (2003) supra). Prothrombin solution in 50 mM Tris, 150 mM NaCl, 5 mM Ca$^{2+}$, 0.6% PEG (to limit thrombin adsorption to micro-plates), pH 7.5, was loaded into one sample loop, and pre-assembled prothrombinase complex (factor concentrations same as in stopped flow fluorescence studies) in the same buffer was loaded into another sample loop. The quenching solution was 100 µL of 100 mM Na$_2$EGTA solution, pH 7.5. Aliquots from collected samples were assayed for amidolytic activity using S-2238 in a micro-plate reader (SLT 340ATTC, SLT Instruments, Hillsborough, N.C.), and the concentration of active site (II$_a$ plus MzII$_a$) was determined by comparing the initial rate of S-2238 hydrolysis to a standard curve obtained with active-site-titrated thrombin as described (Wu, et al. (2002) supra). MzII$_a$ and thrombin formation were distinguished by incubating the reaction mixture aliquot for 1 minute at room temperature in the presence of heparin (10 µg/ml) and antithrombin III (300 nM) to selectively block the thrombin but not the MzII$_a$ active site (Rosing, et al. (1986) *J. Biol. Chem.* 261(9):4224-8). The initial rate of thrombin formation was obtained by subtracting the rate of MzII$_a$ appearance from the initial rate of total active site formation.

Fluorescence Titration of DEGR-X$_a$ by FV$_{a2}$ in the Presence of C6PS. These measurements were carried out with a SLM 48000® spectrofluorometer (SLM Aminco, Urbana, Ill.) as described (Majumder, et al. (2002) supra). The cuvette was initially charged with a solution of 1 nM DEGR-X$_a$ and 5 nM FV$_a$ in order to "condition" the cuvette (Boskovic, et al. (2001) supra). The cuvette contained 0.95 mL of 1 nM DEGR-X$_a$ and 400 µM C6PS in 50 mM Tris, 0.1 M NaCl, 5 mM Ca$^{2+}$ at pH 7.5. FV$_{a2}$ was added from a stock solution, the mixture was incubated for at least 2 minutes, and several intensity readings were taken, averaged, and corrected for dilution.

Analysis of Prothrombin Activation by SDS-PAGE The reaction mixtures were as described in the chemical quench experiments. Aliquots of 40 µL were taken at 0.5, 0.75, 1, 1.25 and 1.5 seconds and subjected to gel electrophoresis (1.5 mm of 12% polyacrylamide) with and without reduction with 5% (v/v) 2-mercaptoethanol (Laemmli (1970) *Nature* 227(259): 680-5). Protein bands were visualized by staining with Colloidal Coomassie Blue (Mitra, et al. (1994) *Anal. Biochem.* 223(2):327-9) and protein bands quantified as described (Wu, et al. (2002) supra; Weinreb, et al. (2003) supra).

Native Gel Electrophoresis. This method has been used to document the association of blood coagulation proteins in solution (Majumder, et al. (2002) supra; Majumder, et al. (2003) supra). A mixture of 1 nM FX$_a$ and 1 nM FV$_a$ was incubated at 37° C. for 2 minutes in the presence and absence of 400 µM C6PS and the two samples were run together with known marker proteins (270 kiloDalton-14.2 kiloDalton; SIGMA, St. Louis, Mo.) on five gels (5, 6, 6.5, 7, and 8% total acrylamide with bisacrylamide/acrylamide being 1/29 in all cases) in a BIORAD® MINI-PROTEAN® II minigel apparatus (BIORAD® Corp., Hercules, Calif.) and stained with colloidal Coomassie blue (Mitra, et al. (1994) supra). FX$_a$ and FV$_a$, at these same concentrations and in the presence of 400 µM C6PS, were run separately as controls. Protein retardation coefficients, which depend to a good approximation only on the hydrodynamic size and shape of the protein, were determined for both the marker and unknown proteins (Ferguson (1964) *Metabolism* 13:985-1002). A log-log plot of the retardation coefficient against the molecular weights of the marker proteins produced a linear curve from which the molecular weight of the FV$_a$•FX$_a$ complex was determined from its measured retardation coefficient (Bryan (1977) *Anal. Biochem.* 78(2):513-9).

Analysis of FV$_{a2}$-FX$_a$ Binding. The total concentration of DEGR-X$_a$•V$_a$ complex at any given C6PS concentration ([DEGR-X$_a$•V$_a$]$_{(C6PS)}$) is given by the familiar expression for two-species binding:

$$[DEGRX_a \cdot V_a]_{(C6PS)} = \frac{[DEGRX_a]_{tot} + [V_a]_{tot} + K_d^{eff} - \sqrt{([DEGRX_a]_{tot} + [V_a]_{tot} + K_d^{eff})^2 - 4[DEGRX_a]_{tot}[V_a]_{tot}}}{2} \quad (1)$$

where the concentration terms all are "total" concentrations of each species in a sample. The change in fluorescence signal of DEGR-X$_a$ was taken as proportional to the fraction of DEGR-X$_a$ bound to FV$_a$:

$$\frac{F - F_0}{F_{SAT} - F_0} = \frac{[DEGR - X_a \cdot V_a]_{(C6PS)}}{[DEGR - X_a]_{tot}} \quad (2)$$

where the fluorescence parameter F$_0$ was fixed as the DEGR-X$_a$ fluorescence before titration began and F$_{SAT}$ is the fluorescence at saturation, which was obtained along with K$_d^{eff}$ by non-linear regression of the data as described in (Majumder, et al. (2002) supra).

Kinetic analysis. To determine the kinetic constants for the first two proteolytic events (reactions a and c, see FIG. 2), three experimentally-determined time courses (thrombin formation, MzII$_a$ appearance, Pre2 appearance) were fitted according to a steady state kinetic scheme that assumed a parallel, sequential reaction mechanism (FIG. 4), as described (Wu, et al. (2002) supra). A fraction, f, of prothrombin consumption was considered to convert directly to thrombin without the escape of an intermediate from the membrane-enzyme-cofactor complex (termed channeling) (Boskovic, et al. (2001) supra; Wu, et al. (2002) supra; Weinreb, et al. (2003) supra). All three sets of data were fitted simultaneously by adjusting first order rate constants R$_a$ (for reaction A, FIG. 2), R$_c$ (reaction C) and R$_e$ (reaction E), while R$_b$ and R$_d$ (for reactions B and D) were fixed at the values determined independently herein. Competition of prothrombin and MzII$_a$ substrates for enzyme active sites was explicitly taken into account during global fitting of the data using the SCoP Simulation Program (Simulations Resources Inc., Berrin Springs, Mich.), as described (Wu, et al. (2002) supra).

Complex Assembly

Figure 2:
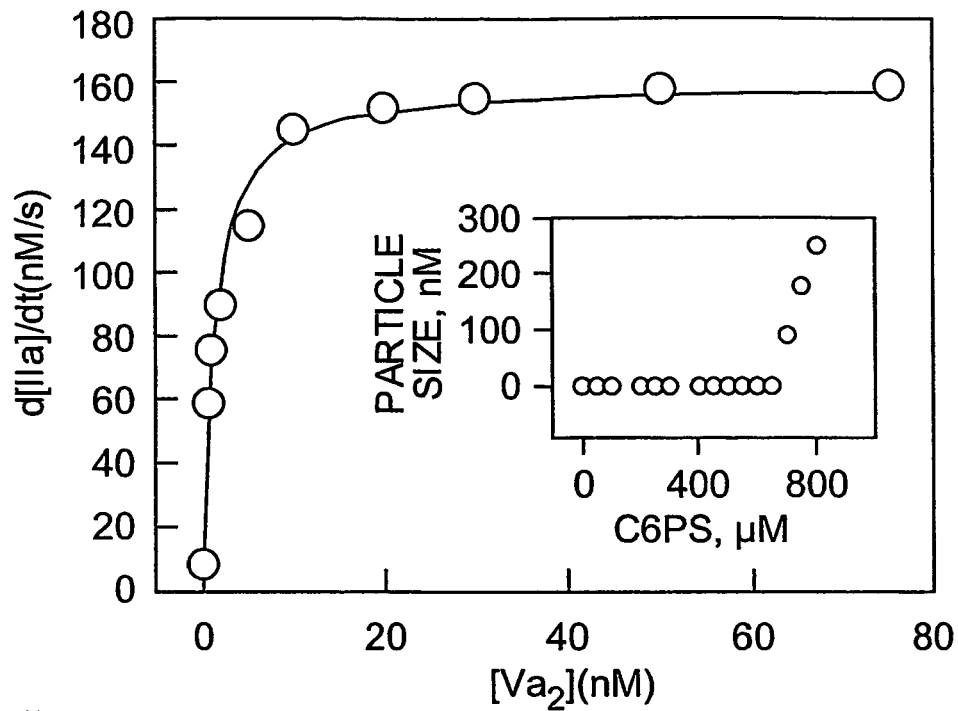
FIG. 2 shows assembly of the prothrombinase complex as monitored by the rate of thrombin formation in the presence of C6PS. The initial rate of thrombin formation was monitored by DAPA fluorescence. Stopped flow fluorescence measurements were performed at 37° C. with final mixing chamber concentrations of 1 µM prothrombin, 5 µM DAPA, 1 nM factor $X_a$, 400 µM C6PS and various concentrations of factor $V_{a2}$ (Panel A) or $V_{a1}$ (Panel B) in 50 mM Tris-HCl (pH 7.5), 150 mM NaCl, 5 mM $CaCl_2$. The initial rates were fit to a single binding site model as described herein to determine the $K_d^{eff}$ of factor $X_a$ binding to factor $V_{a2}$ in presence of 400 µM C6PS (2.4±0.3 nM). The inset to Panel A shows the size of aggregates detected by quasi-elastic light scattering at increasing concentrations of C6PS under the conditions of these experiments. The abrupt appearance of aggregates at 700 µM C6PS defines the critical micelle concentration under these experimental conditions.
Figure 2:
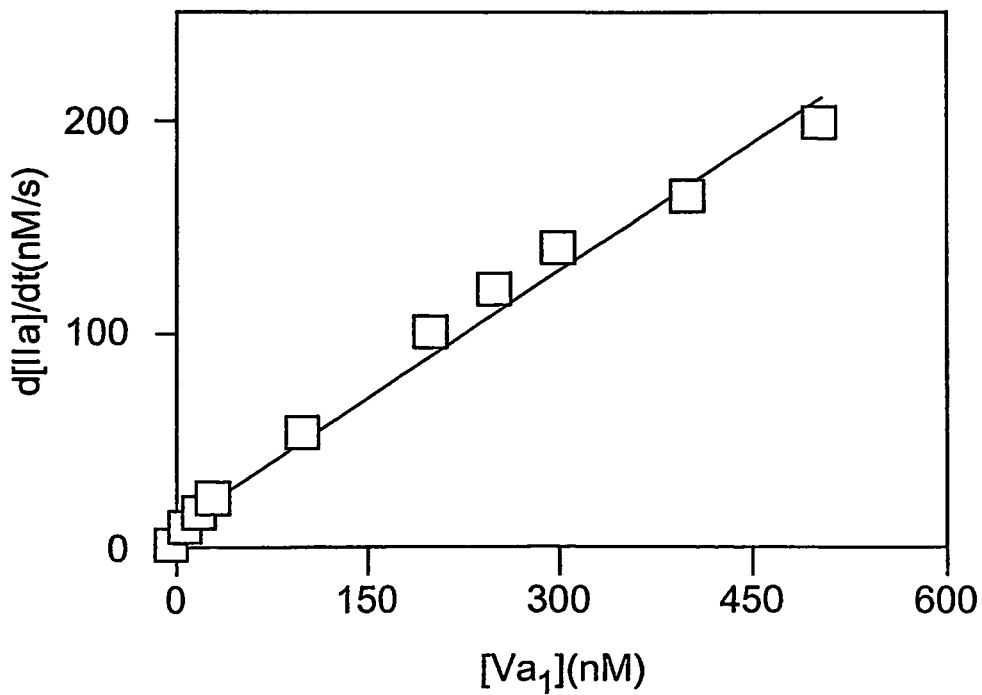

Initial rates of prothrombin activation by FX$_a$ as monitored by DAPA fluorescence are shown in FIG. 2 as a function of added FV$_{a2}$ (Panel A) and FV$_{a1}$ (Panel B) in the presence of 400 µM C6PS. The rate saturated for FV$_{a2}$ (Panel A) but did not saturate for FV$_{a1}$ (Panel B). The apparent K$_d$ of the FV$_{a2}$ (2 nM) interaction with FX$_a$ was at least 300-fold tighter than for FV$_{a1}$ (>1 µM). This result demonstrates that these two forms of human FV$_a$ have very different abilities to interact with FX$_a$ in the presence of C6PS, and that they also have different cofactor activities when bound to FX$_a$ in the presence of soluble C6PS. The tight binding of FV$_{a2}$ with FX$_a$ in the presence of C6PS led to the use FV$_{a2}$ as the cofactor in all the kinetic experiments described herein. The inset to FIG. 2 (Panel A) shows the size of aggregates detected at different C6PS concentrations under the conditions used for the kinetic experiments (1 nM FX$_a$ and 5 nM FV$_{a2}$). From this, it was determined that the critical micelle concentration (CMC) of C6PS in the presence of factors X$_a$ and V$_{a2}$ was roughly 700 µM. No aggregates were detectable below this concentration.

Figure 3:
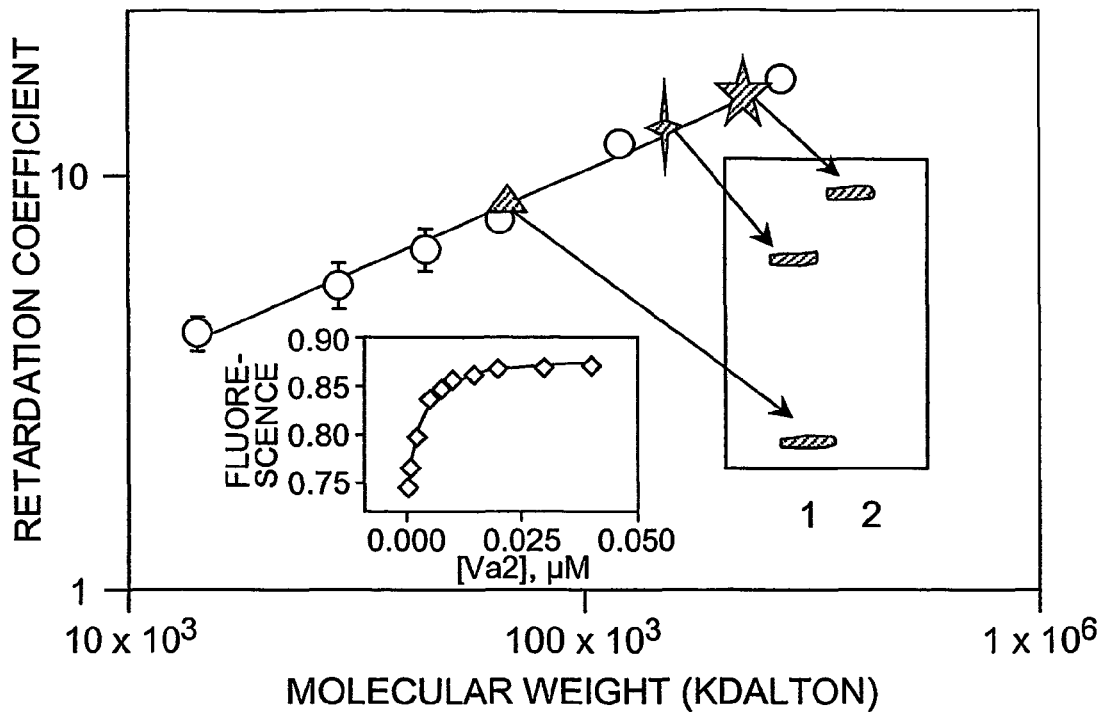
FIG. 3 shows the characterization of the complex formed by $FX_a$ and $FV_{a2}$ in the presence of soluble C6PS. A mixture of $FX_a$ and $FV_{a2}$ in the absence (lane 1 of gel) and presence (lane 2) of 400 µM C6PS (5 mM $Ca^{2+}$) was analyzed by native polyacrylamide gel electrophoresis on a standard 6% gel (Majumder, et al. (2002) supra). A log-log plot of retardation coefficients versus molecular mass of different reference proteins is also shown (open circles). Points have been added to this plot for retardation coefficients obtained for $FX_a$ (triangle) or $FV_{a2}$ (4-point star) in the absence of C6PS, and of the $FX_a \cdot FV_{a2}$ complex (5-point star) formed in the presence of C6PS. The apparent molecular weight of the complex, as identified from this plot, was 224±3.7 kilodaltons. The inset at lower left (diamonds) shows the fluorescence of [5-(dimethylamino)-1-napthalenesulfonyl]glutamylycylarginyl chloromethyl ketone (DEGR)-modified $X_a$, prepared using standard methods (Majumder, et al. (2002) supra), as a function of added $FV_{a2}$, yielding an effective dissociation constant ($K_d^{eff}$) of 2±0.2 nM.

The tight binding of human FV$_{a2}$ to active site-labeled human FX$_a$ (DEGR-X$_a$) in the presence of 400 µM C6PS is also illustrated in the left inset of FIG. 3, which shows the fluorescence intensity of DEGR-X$_a$ as a function of the concentration of added FV$_{a2}$. FIG. 3 also shows a Ferguson plot (Ferguson (1964) supra) of retardation coefficients of standard proteins and of FX$_a$ and FV$_{a2}$ in the absence (lane 1) and presence (lane 2) of C6PS. The appearance of a single, well-defined band in lane 2 (FIG. 3; 5-pointed star in the Ferguson plot) confirmed that FV$_{a2}$ and FX$_a$ formed a well-defined complex in the presence of 400 µM C6PS (molecular mass of 224±3.7 kiloDalton as determined by the Ferguson method of analysis). In the absence of C6PS, no complex appeared (lane 1, right inset of FIG. 3), and the measured molecular weights were 45.9±1.2 and 176.45±2 kiloDalton for FX$_a$ (triangle) and FV$_{a2}$ (4-pointed star), respectively, compared with reported values of 46 kiloDalton for FX$_a$ (Leytus, et al. (1986) *Biochemistry* 25(18):5098-102) and 177 kilodalton for FV$_{a2}$ (Kane and Majerus (1981) supra). The molecular masses of factors V$_{a2}$ and X$_a$ were also measured in the presence of 400 µM C6PS (to saturate FV$_{a2}$ and saturate the regulatory site in FX$_a$) to obtain 178.5±1.4 and 46.6±1 kiloDalton, respectively. These molecular masses are consistent with these proteins binding 4.2 and 1.5 molecules of C6PS, respectively, based on assuming the molar volume of C6PS is that of protein (0.76 cm$^3$/g). The stoichiometries of C6PS binding to these proteins at saturation, based on direct equilibrium dialysis methods, are 4 and 2, respectively (Zhai, et al. (2002) supra; Banerjee, et al. (2002) supra). These results confirm both the ability of the Ferguson analysis to report accurate molecular weights for the proteins of the prothrombinase complex as well as the ability of the Ferguson method to provide reasonable estimates of the numbers of C6PS molecules bound to these proteins even when gels were run in the presence of C6PS and referenced to standard proteins not bound to C6PS.

Soluble Complex vs. Lipid Aggregate

It is reasonable to ask whether the complex involves binding of FV$_{a2}$ to FX$_a$ to a C6PS aggregate or micelle. First, C6PS micelles were detected by quasi-elastic light scattering and ANS fluorescence (Koppaka, et al. (1996) supra) under the conditions of this experiment only at 700 µM C6PS and above which is well above the concentration used in the experiments herein. Quasi-elastic light scattering detected the minimal micelle that one would predict for C6PS (~200 monomers) (Koppaka, et al. (1996) supra). C6PS micelles formed in the presence of the X$_a$-V$_{a2}$ complex contain ~17,000 to 125,000 monomers (depending on C6PS concentration, see inset to FIG. 2) and thus are much easier to detect. Thus, quasi-elastic light scattering is certainly sufficient to detect C6PS micelles if they form under the conditions of experiments conducted herein. Since micelles are aggregates, their formation resembles a phase transition, i.e., amphipaths exist as monomers in solution up to a well-defined critical micelle concentration (CMC) and then as micelles in equilibrium with monomers above that concentration (Tanford (1973) The Hydrophobic Effect, John Wiley & Sons, New York). Thus, by working well below the CMC, the possibility that even a small concentration of micelles contributes to the kinetics of prothrombin activation was minimized.

The possibility that the FX$_a$•FV$_{a2}$ complex might form on some hypothetical "micro-surface" that might nucleate on the protein complex was examined. The active FX$_a$•FV$_{a2}$•C6PS complex observed in kinetic experiments described below has a molecular mass of 224±3.7 KDalton (see FIG. 3). This molecular mass is consistent with a stoichiometry of 1:1:3.4±7.7 (X$_a$:Va2:C6PS). The error in this measurement (i.e., ±7.7 C6PS) is such that the exact number of C6PS molecules bound to the complex could not be determined but, within this error bar, it is likely that no more than 11 and not less than 0 C6PS molecules are bound to the complex. Based on the stoichiometries for C6PS binding to FX$_a$ (2) and FV$_{a2}$ (4), as determined by equilibrium dialysis (Srivastava, et al. (2002) supra; Zhai, et al. (2002) supra), this number is most likely 5 to 6 C6PS molecules. It is unlikely that only 5-6 (at most 11) C6PS molecules could form a surface with their head groups accessible to water (and X$_a$ and V$_{a2}$) and their chains buried out of water as such an arrangement would be thermodynamically unstable. Even if such a small aggregate were possible, an aggregate of this size would not be sufficient to assemble a membrane-like prothrombinase, since roughly 25 lipids are minimally required to accommodate each of these proteins to membrane surfaces (Cutsforth, et al. (1989) *Biochemistry* 28(18):7453-61; Cutsforth, et al. (1996) supra). Further, the 5-6 C6PS molecules are bound to very different regions of factor X$_a$ (one in EGF pair and one in catalytic domain (Srivastava, et al. (2002) supra)) and factor V$_a$ (two in heavy chain, two in light chain with one of these in the C2 domain (Srivastava, et al. (2001) *Biochemistry* 40(28):8246-55; Zhai, et al. (2002) supra). Thus, it is unlikely that these few lipids could cluster into any kind of a surface, even a hypothetical micro-surface. The results provided herein demonstrate that the $FV_{a2} \cdot FX_a$ complex forms in solution in response to binding of individual C6PS molecules to $FX_a$ and $FV_{a2}$ rather than to assembly of this complex on aggregates of C6PS.

Kinetics of Prothrombin Activation

Figure 4:
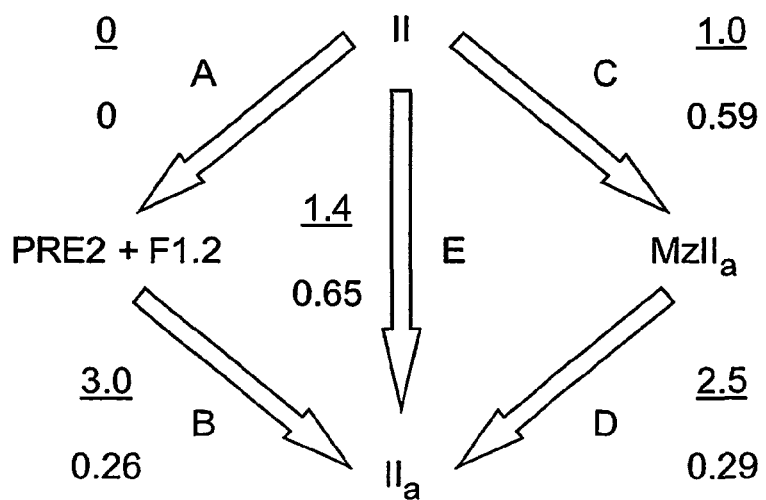
FIG. 4 shows a schematic representation of human prothrombin (II) activation. Two peptide bonds {$Arg^{273}$-$Thr^{274}$} and {$Arg^{322}$-$Ile^{323}$} in prothrombin are cut by factor $X_a$ for activation to thrombin ($II_a$) thereby creating two possible pathways of activation (A&B and C&D) and two possible released intermediates (Pre2 and $MzII_a$). A third possible pathway of activation (E) occurs when no intermediate is released ("channeling" or processive activation). The rate constants ($k_{cat}/K_M$ in units of $10^8$ $M^{-1}S^{-1}$) for different steps as catalyzed either by the $FX_a$-$FV_{a2}$-C6PS complex (underlined text; results described herein) or by the $FX_a$-$FV_a$-PS/PC membrane complex (normal text; Weinreb, et al. (2003) *J. Biol. Chem.* 278(8):5679-84) are shown.
Figure 5:
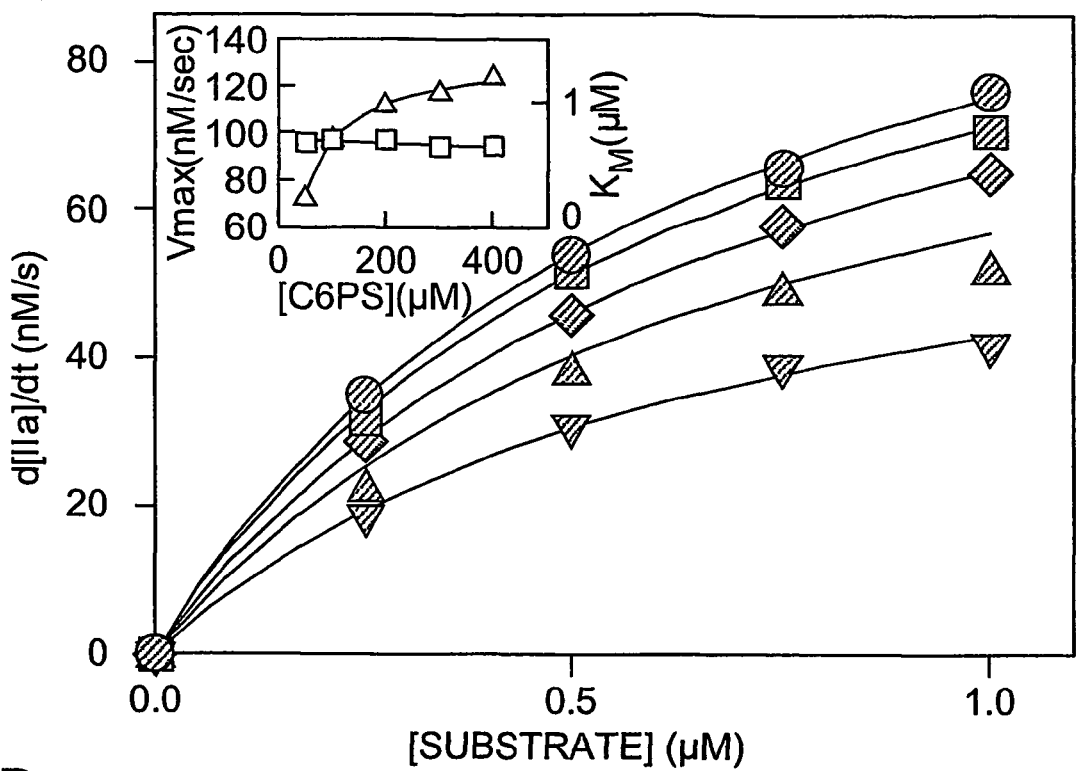
FIG. 5 shows the initial rates of thrombin formation from intermediates as a function of substrate concentration. Activation was initiated by stopped-flow mixing of equal volumes of substrate and DAPA in one syringe with prothrombinase complex in another syringe. Substrates were $MzII_a$ (Panel A) and an equimolar mixture of Pre2 & F1.2 (Panel B). The concentration of C6PS was: 50 µM (inverted triangles), 100 µM (triangles), 200 µM (diamond), 300 µM (square), and 400 µM (circle). The kinetic parameters $V_{max}$ (open triangles) and $K_M$ (open squares) for the conversion of $MzII_a$ and Pre2+ Fragment 1.2 to thrombin are plotted versus C6PS concentration in the insets to Panels A and B, respectively.
Figure 5:
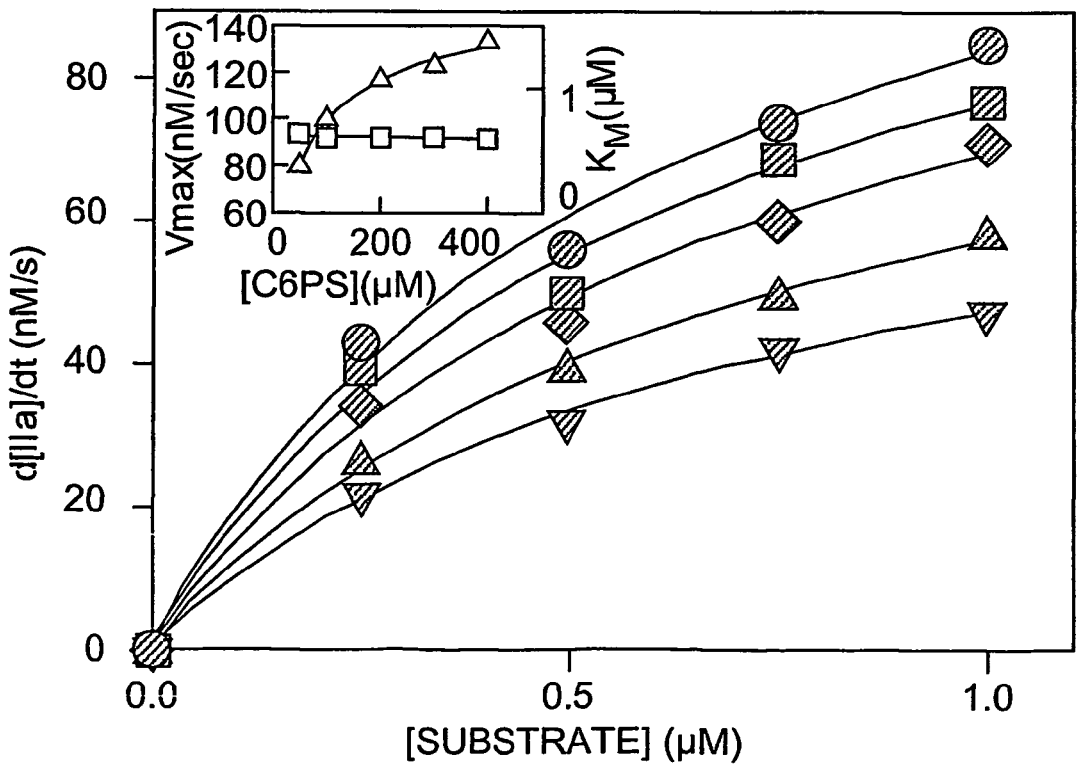

To compare the activities of C6PS- and membrane-assembled prothrombinase, the second order rate constants for all five possible reaction steps of prothrombin activation were determined (FIG. 4). Two of these create the intermediates $MzII_a$ and Pre2+F1.2 (reactions C and A in FIG. 4), and two of these (reactions B and D) convert the intermediates to thrombin. A fifth pathway (E in FIG. 4) converts prothrombin to thrombin without release of an intermediate (channeling or processive activation) (Boskovic, et al. (2001) supra; Wu, et al. (2002) supra; Weinreb, et al. (2003) supra). The activation of $MzII_a$ and Pre2+F1.2 to thrombin reflects cleavage of individual peptide bonds (see legend to FIG. 4). The time-courses of thrombin formation from $MzII_a$ or Pre2&F1.2 were determined by stopped-flow experiments as described. Analysis of plots of the initial rates of thrombin formation (proportional to DAPA fluorescence change) measured at different lipid concentrations as a function of increasing concentrations of $MzII_a$ (FIG. 5, Panel. A) and Pre2&F1.2 (FIG. 5, Panel B) in terms of the Michaelis-Menten model was conducted to obtain the $K_M$ (squares) and $V_{max}$ (triangles) that define the kinetics of $MzII_a$ and Pre2&F1.2 activation at various C6PS concentrations (insets to FIG. 5, Panels A and B, respectively). To compare the C6PS-assembled prothrombinase to the known kinetic behavior of the membrane-assembled prothrombinase, second order rate constants ($k_{cat}/K_M$) were needed. To calculate these from $V_{max}/K_M$, an estimate of the fraction of total $FX_a$ incorporated into prothrombinase was required. To obtain this, the $K_d^{eff}$ for the $FX_a$-$FV_{a2}$ interaction (FIG. 3) was used to calculate, using Equation 1, the effective concentration of the assembled prothrombinase enzyme, $E_{bound}$, as has been described (Majumder, et al. (2002) supra). Effective $k_{cat}$'s were calculated as $V_{max}/E_{bound}$, leading to the $k_{cat}/K_M$ values summarized in FIG. 4.

DAPA is a weak competitive inhibitor of $FX_a$ (Nesheim, et al. (1979) supra). Despite this, it has been shown that it provides rates of prothrombin activation in the presence of PS/PC membranes equivalent to those detected by activity measurements (Wu, et al. (2002) supra; Weinreb, et al. (2003) supra). To test whether DAPA influenced the activity of $FX_a$ in the presence of C6PS, the expected DAPA fluorescence was calculated based on the rate of appearance of thrombin and $MzII_a$, as detected by synthetic substrate assay as recorded in FIG. 6A. This calculation has been described (Wu, et al. (2002) supra) and its results, as applied to the data herein, are shown in the inset to FIG. 6A (filled circles) along with an experimental time-course of DAPA fluorescence change (open diamonds) reflecting prothrombin activation. Similar results were obtained at the other prothrombin concentrations examined. These results demonstrate that DAPA reflects $FX_a$ activity exactly as reflected by other methods in the absence of DAPA. Thus, the concentration of DAPA used herein does not influence $FX_a$ activity to a measurable extent.

Figure 6A:
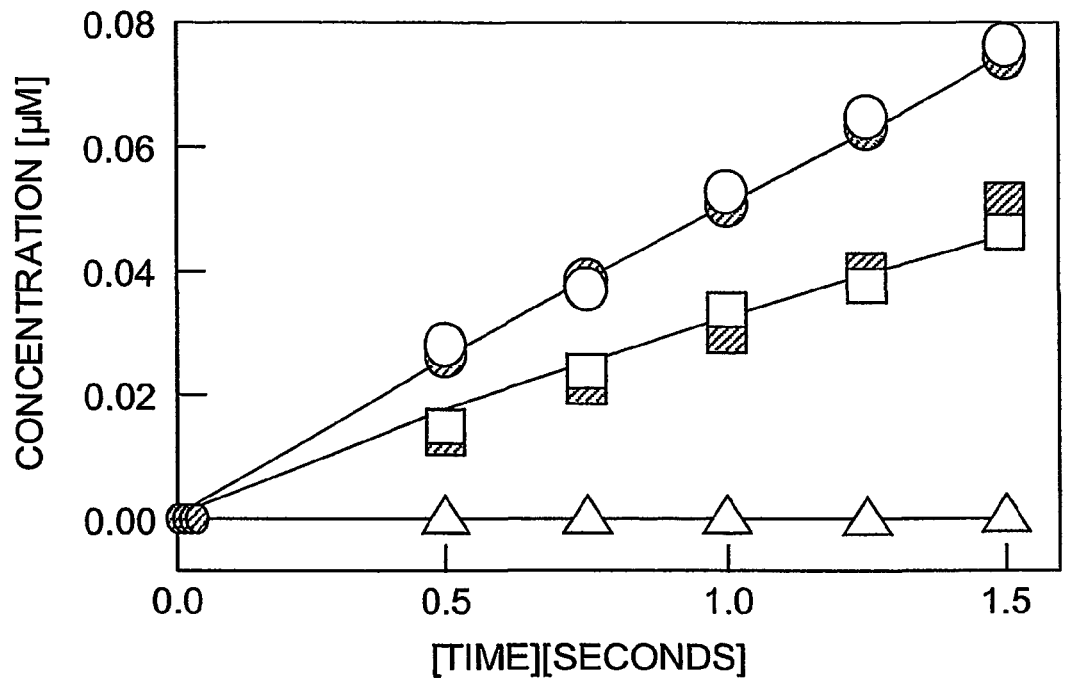
FIG. 6A shows the best fits of simulations to observed initial prothrombin proteolysis time courses. Prothrombin (0.5 µM) proteolysis catalyzed by Factor $X_a$ (1 nM) in the presence of 5 mM $CaCl_2$, factor $V_{a2}$ (5 nM), and 400 µM C6PS, was monitored at 37° C. either by means of thrombin (circles) and $MzII_a$ (squares) activity (shaded symbol), or by means of SDS-PAGE and densitometry (open symbols). The time course of Pre2 formation detected by SDS-PAGE is presented as open triangles. The inset shows the rate of change of DAPA (2.5 µM) fluorescence under the same conditions (open triangles) along with DAPA fluorescence calculated (Wu, et al. (2002) supra) from the activity data shown in this figure.
Figure 6B:
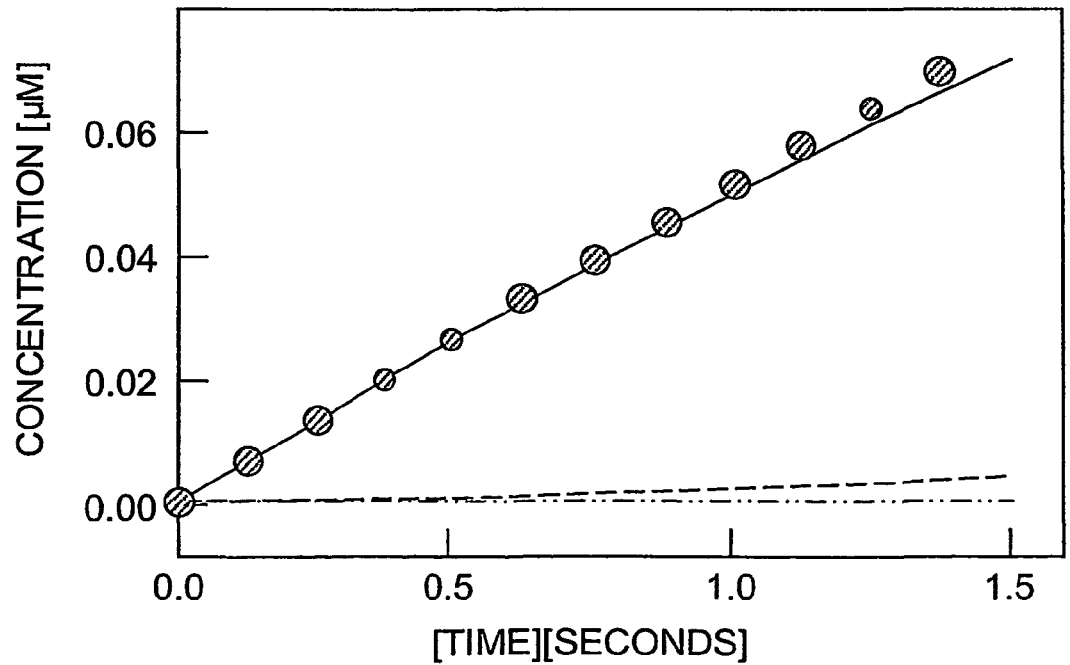
FIG. 6B shows the calculated time courses of thrombin formed via the Pre2 (dot dashed line), the $MzII_a$ (dashed line), and the channeling (solid line) pathways, with shaded circles showing the experimental time course for total thrombin formation.

To complete the kinetic analysis of the C6PS-assembled prothrombinase, rate constants for the initial steps shown in FIG. 4 (reactions A and C) as well as for the channeling pathway (reaction E) were needed. The rates of these reactions are difficult to measure directly, therefore an approach described earlier for the membrane-assembled prothrombinase (Wu, et al. (2002) supra; Weinreb, et al. (2003) supra) was used. FIG. 6A shows initial time courses of thrombin (circles) and $MzII_a$ (squares) appearance measured by the synthetic substrate assay (closed symbols) as well as these time courses and that of Pre2 appearance (triangles) measured by SDS-PAGE (open symbols). As the rate of thrombin formation was much greater than the rate of $MzII_a$ appearance at 400 μM C6PS, either significant thrombin formation occurred through the Pre2 pathway or a large fraction of $MzII_a$ and/or Pre2 was rapidly processed directly to thrombin, and thus not detected as released intermediate. Because no Pre2 formation was detected, the first possibility can not be excluded, and it must be that a fraction of intermediate(s) is processed directly to thrombin (reaction E in FIG. 4) just as occurs for the membrane-assembled prothrombinase (Weinreb, et al. (2003) supra). To determine quantitative estimates of rate constants for reactions C and E, the data in FIG. 6A was fit, as described (Wu, et al. (2002) supra; Weinreb, et al. (2003) supra), with rate constants for reactions B and D fixed at the values shown in FIG. 4. The resulting rate constants for reaction A, C, and E are also summarized in FIG. 4. Comparison of these rate constants with known rate constants (Banerjee, et al. (2002) supra; Wu, et al. (2002) supra; Weinreb, et al. (2003) supra) establishes that the C6PS- and membrane-assembled complexes are similar in two respects: they both cause significant fractions (58% for C6PS and 50-60% for membranes) of prothrombin to be converted directly ("channeled") to thrombin; and they both direct activation nearly exclusively through the $MzII_a$ intermediate. Because the rate of $MzII_a$ conversion to thrombin is roughly the same as the rate of reaction E, nearly all thrombin that is initially formed by the C6PS-assembled complex is formed via reaction E (channeling; FIG. 6B), just as for the membrane complex (Weinreb, et al. (2003) supra).

Despite these similarities, there is an unexpected difference between the membrane- and C6PS-complexes in that activation is roughly an order of magnitude faster for the C6PS-assembled complex. This may be because the C6PS-assembled complex is actually more active or because $FV_{a2}$ is a somewhat better cofactor in solution than is the natural $FV_{a1}$&$FV_{a2}$ mixture on a membrane. To distinguish between these possibilities, the initial rates of thrombin plus $MzII_a$ formation from prothrombin were determined in the presence of soluble C6PS and 25% PS/PC membranes under identical experimental conditions, but with whole $FV_a$ or $FV_{a2}$ as cofactors. The overall $k_{cat}/K_M$ estimated from these measurements for prothrombin activation by $FX_a$ and $FV_{a2}$ in the presence of C6PS ($2.2 \times 10^8$ $M^{-1}sec^{-1}$) was two-fold smaller than in the presence of membranes ($4.4 \times 10^8$ $M^{-1}sec^{-1}$). Overall activation by the membrane-complex containing $FV_{a2}$ was roughly 40-fold faster than for that containing $FV_a$ ($k_{cat}/K_M \sim 10^7$ $M^{-1}sec^{-1}$), confirming that $FV_{a2}$ is a somewhat better cofactor than the natural mixture, even on a membrane. To make another comparison of the activities of the $FV_{a2}$ and $FV_a$ cofactors, the rates of $MzII_a$ activation by $FX_a$ on PS/PC membranes in the presence of $FV_{a2}$ ($3.0 \times 10^8$ $M^{-1}sec^{-1}$) or $FV_a$ ($2.9 \times 10^7$ $M^{-1}sec^{-1}$) was compared, confirming that $FV_{a2}$ is the better cofactor on a membrane even when only one bond is cut. The rate of this reaction for the C6PS-assembled $FX_a$-$FV_{a2}$ complex ($3.5 \times 10^8$ $M^{-1}sec^{-1}$) is nearly identical to the rate seen with the same cofactor on membranes. Since these solution and membrane complexes are nearly identical with respect to this single-step reaction and because the extent of channeling is nearly identical for the membrane- and C6PS-assembled complexes, the minor two-fold increase in overall activation rate for the membrane complex likely reflects slightly improved delivery of membrane-bound prothrombin to membrane-bound complex on the membrane surface. This possible effect of a membrane surface has been discussed (Rosing, et al. (1980) supra; Nesheim, et al. (1984) *J. Biol.*

Chem. 259(3):1447-53; Giesen, et al. (1991) supra), but the magnitude of the effect has generally been assumed to be much larger than that which is reported herein.

Example 2

Factor X-Activating Complex

Results

Figure 8:
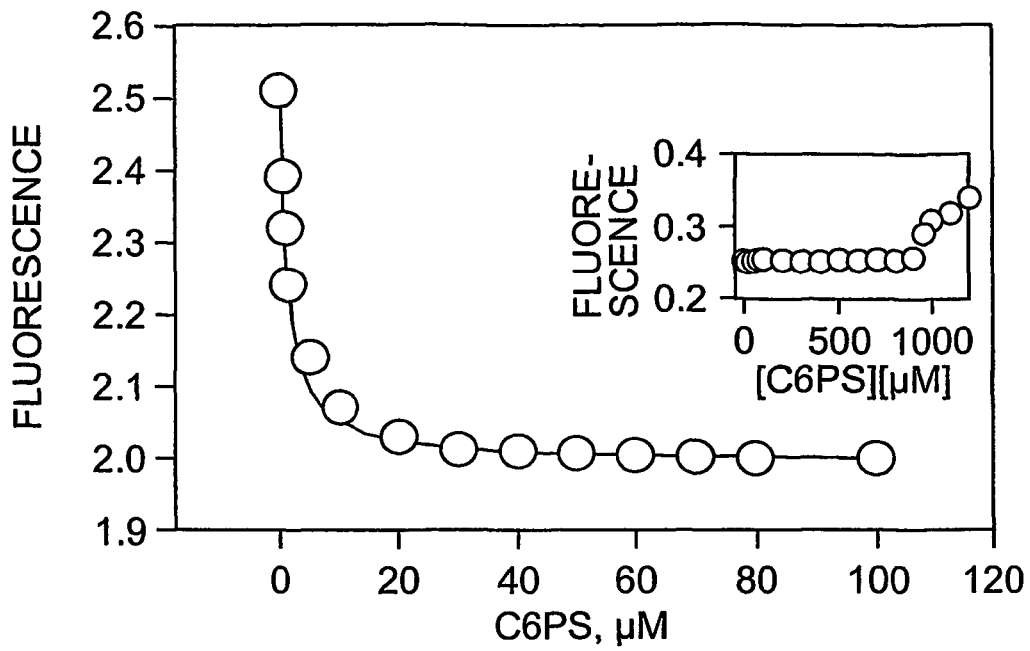
FIG. 8 shows binding of C6PS to Factor $IX_a$ as detected by intrinsic fluorescence. Integrated intrinsic fluorescence of 0.20 µM factor $IX_a$ in 50 mM Tris, 150 mM NaCl, 5 mM $CaCl_2$, and 0.6% PEG, pH 7.5 was measured as a function of C6PS concentration at 22° C. to follow C6PS binding. The inset shows the fluorescence titration of ANS in the presence of 200 nM factor $IX_a$ and calcium with the sudden increase of fluorescence indicating C6PS CMC.
Figure 9:
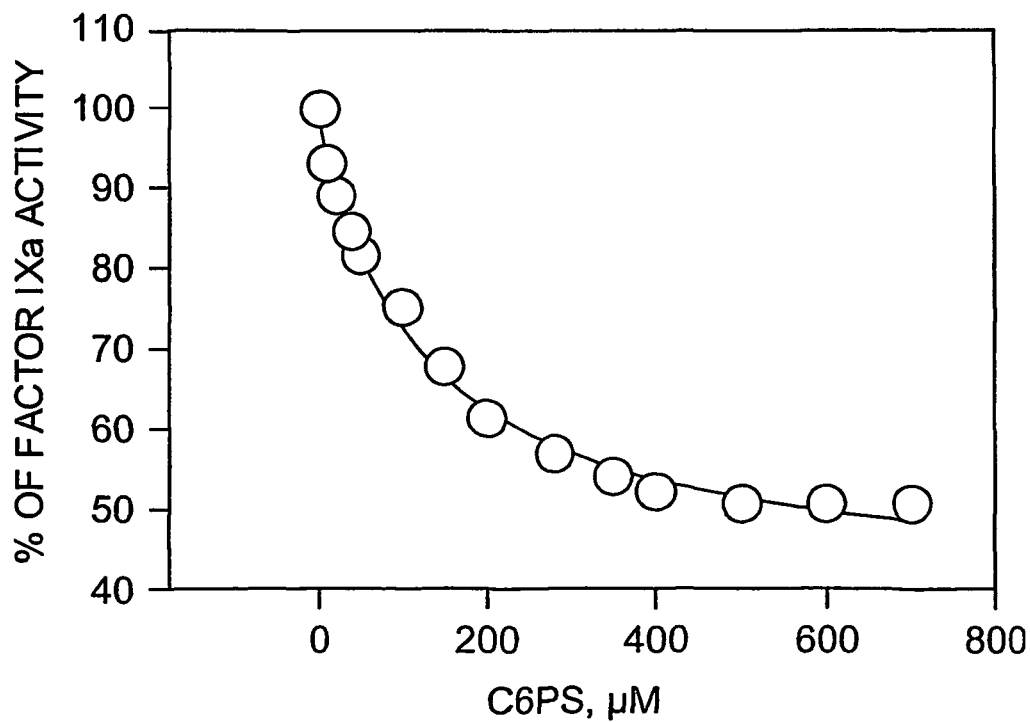
FIG. 9 shows the amidolytic activity of $IX_a$ (300 nM) in 20 mM Tris, 150 mM NaCl, 5 mM calcium and 0.6% PEG. The assay was conducted in the presence of 1 mM Leu-PHG-Arg-pNA.AcOH and increasing concentrations of C6PS.

FIG. 8 shows that the intrinsic tryptophan fluorescence of factor $IX_a$ changes with the addition of soluble C6PS in the presence of 5 mM calcium, suggesting that C6PS binds to factor $IX_a$. The curve was fitted by a single binding site model (Equations 1 & 2 in Example 1) to obtain a stoichiometric $K_d$ of about 1.3 μM. In order to make sure that a molecular form of C6PS, and not micelles, was causing this effect, the CMC of C6PS was determined (using ANS as a fluorescent probe) under the same experimental conditions (Koppaka et al. 1997 supra), and it was found to be 950 μM, which is much higher than the highest C6PS concentration used in this experiment (see the inset in FIG. 8). FIG. 9 shows the amidolytic activity (substrate Leu-PHG-Arg-pNA-AcOH, which does not depend on ethylene glycol) of 300 nM factor $IX_a$ in the presence of increasing C6PS concentration. A fit of these data to a single-site binding model gives a $K_d$ of 130 μM. The 2 order of magnitude difference in the two $K_d$ values shows that $IX_a$, like factor $X_a$ (Banerjee (2002) Biochemistry 41 7751), has two binding sites for C6PS. These results also established that factor $IX_a$, also like factor $X_a$ (Koppaka et al. 1997 supra; Majumder et al (2002) Biophysical Journal 84 1238), undergoes changes in its active site upon binding C6PS.

Figure 10:
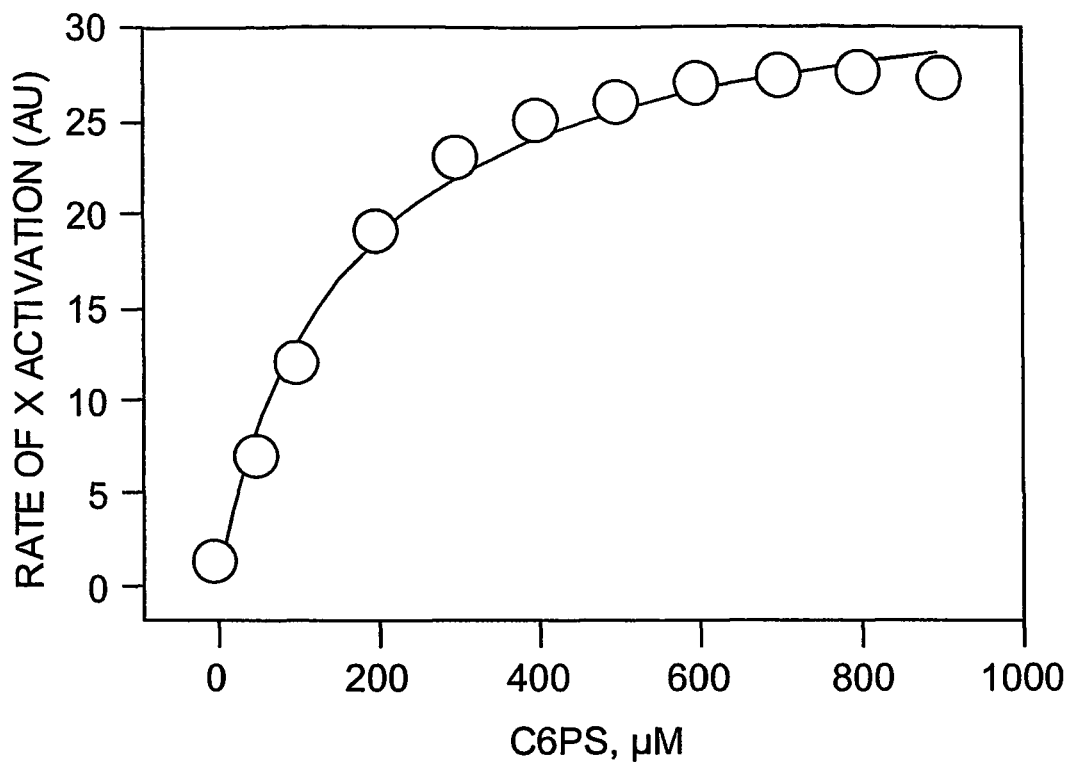
FIG. 10 shows the proteolytic activity of $IX_a$ (10 nM) in 20 mM Tris, 150 mM NaCl, 5 mM calcium and 0.6% PEG. The assay was conducted in the presence of increasing concentrations of C6PS. The hyperbolic fit gives a $K_d$ of 164 µM, which is similar with the $K_d$ obtained in FIG. 9.
Figure 11:
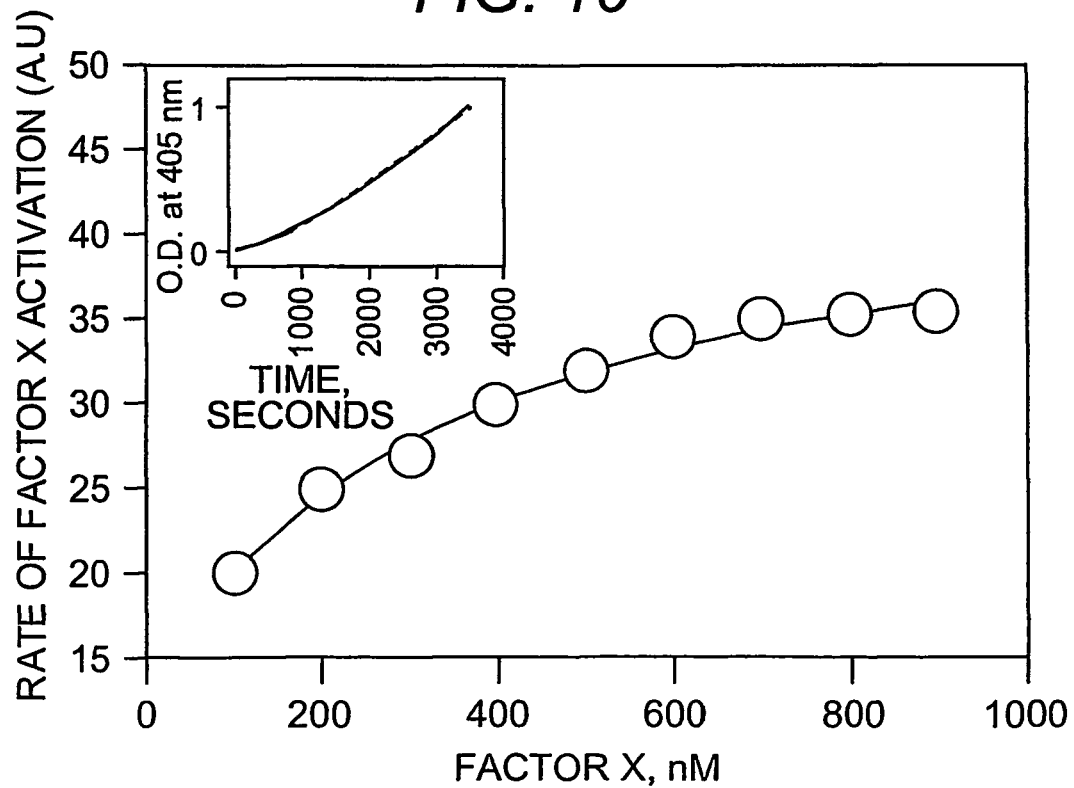
FIG. 11 shows the rate of activation of factor X by factor $IX_a$ in the presence of 700 µM C6PS at different concentrations of factor X. The inset illustrates that the rate of activation of factor X by factor $IX_a$ at 700 µM C6PS is identical to the rate determined in the presence of 20% PS/PC membrane (dashed line), C6PS (solid line).

C6PS promotes the proteolytic activation of factor X by factor $IX_a$, just as it promotes the proteolytic activation of prothrombin by factor $X_a$. FIG. 10 shows the rate of activation of factor X by factor $IX_a$ in the presence of increasing concentrations of soluble phosphatidylserine. The similar $K_d$ values from FIGS. 9 and 10 shows that a common C6PS site in factor $IX_a$ regulates the amidolytic and proteolytic activities. The rate of activation of factor X by factor $IX_a$ in the presence of 700 μM C6PS was monitored at different concentrations of factor X (FIG. 11). The $K_M$ for this reaction was 300 nM, which is the same as that obtained with 20% PS/PC membranes (Larson et al. (1996) J. Biol. Chem. 271 3869). FIG. 11 (inset) shows that the rate of activation of factor X by factor $IX_a$ at 700 μM C6PS is identical to the rate determined in the presence of 20% PS/PC membranes. These results demonstrate that C6PS can substitute completely for PS-containing membranes in the activation of factor X by factor $IX_a$.

Figure 12:
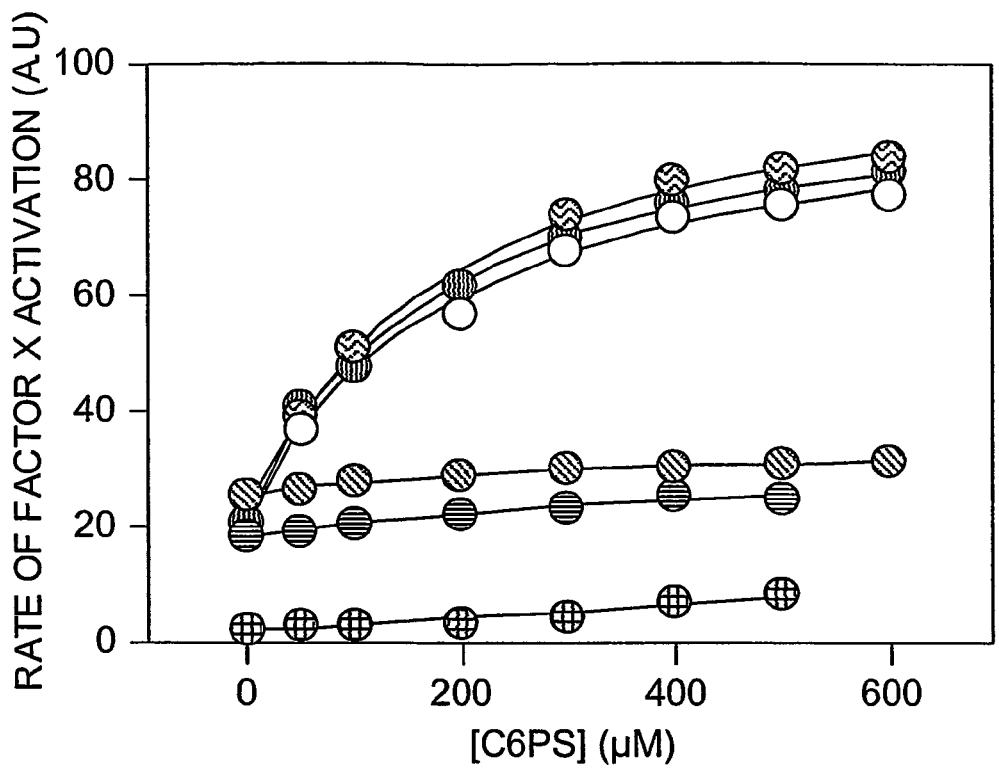
FIG. 12 illustrates the rate of activation of factor X by factor $IX_a$ versus C6PS concentration at different concentrations of calcium 0 mM (cross-hatch shading), 1 mM (horizontal line shading), 2 mM (horizontal line shading), 3 mM (vertical line shading), 4 mM (open), 5 mM (wavy-line shading).

FIG. 12 shows the rate of activation of factor X by factor $IX_a$ versus C6PS concentration at different calcium concentrations. As the concentration of $Ca^{2+}$ increases, the proteolytic activation of factor X by factor $IX_a$ increases as well. Enhancement of factor X activation appears to saturate at a calcium concentration of 3 mM. The data in FIG. 12 demonstrate that both C6PS and calcium enhance proteolytic activation of factor X by factor $IX_a$.

Assembly of an Active $FVIII_a$-$FIX_a$ Complex

One issue is whether SPS can promote assembly of a fully active $VIII_a$-$IX_a$ complex in solution.

Figure 13:
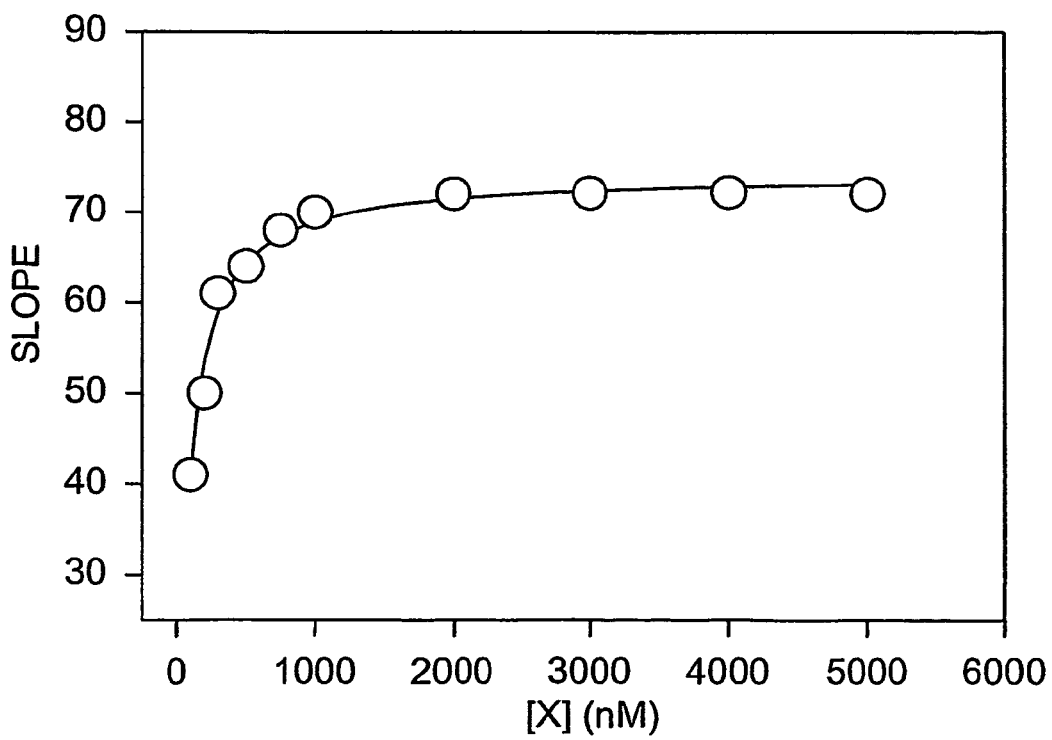
FIG. 13 shows the rate of activation of factor X by 2.5 nM factor $IX_a$ and 10 nM factor $VIII_a$ in the presence of 600 µM C6PS, monitored at different concentrations of factor X.

The rate of activation of factor X by 2.5 nM factor $IX_a$ and 10 nM factor $VIII_a$ in the presence of 600 μM C6PS was monitored at different concentrations of factor X (FIG. 13). The $K_M$ for this reaction was 66 nM, which is similar to that obtained with 30% PS/PC membranes (45 nM) (Larson et al. (1996) J. Biol. Chem. 271 3869). These results showed that the $K_M$ for factor X activation by factor $IX_a$ in the presence of C6PS was reduced by 5-fold with the addition of $VIII_a$.

Assembly of an active $VIII_a$-$IX_a$ complex in the presence of C6PS can also be demonstrated by directly studying the binding of factor $IX_a$ with factor $VIII_a$ in the presence of C6PS, for example, using dansyl-glutamyl-glycyl-arginyl-chloromethylketone labeled factor $IX_a$ (DEGR-$IX_a$).

Example 3

SPS Regulation of Factor $V_a$ Inactivation by APC

Figure 14:
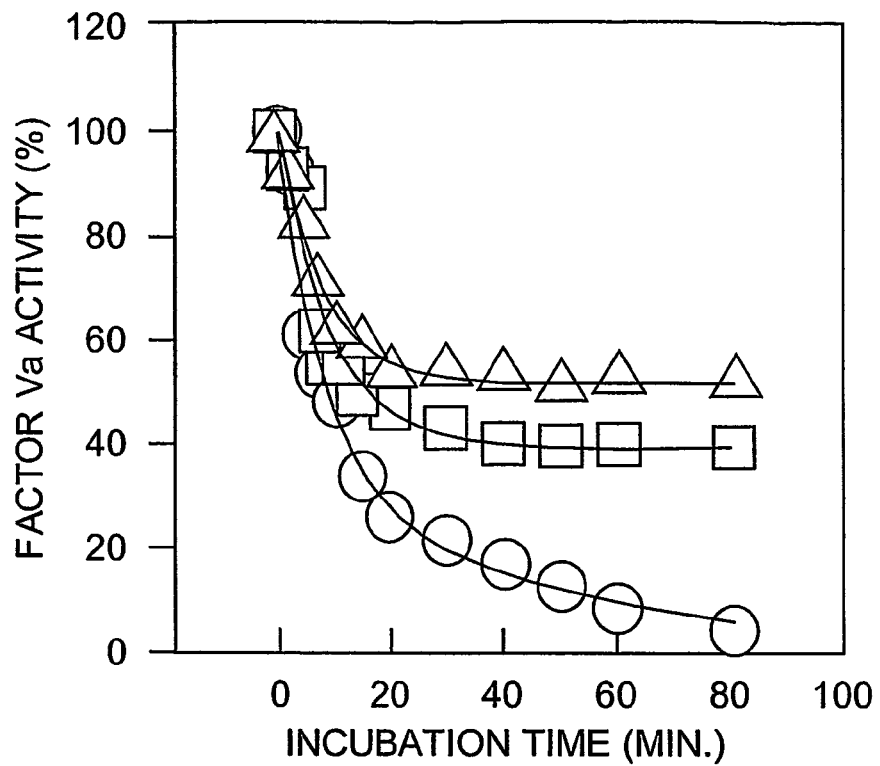
FIG. 14 shows bovine factor $V_a$ (100 nM) incubated with APC (10 nM) in the presence of 200 µM C6PS (circles), 4 µM C6PS (squares), or no C6PS (triangles) at 37° C. Aliquots of this mixture (10 µL) were added at selected time intervals to a cuvette containing prothrombin (1.4 µM), DAPA (5 µM), PCPS vesicle (50 µM), and factor $X_a$ (10 nM) in a total assay volume of 1 mL. The fluorescence intensity of the thrombin-DAPA was monitored with time. Under these conditions, the rate of thrombin formation is proportional to the rate of DAPA fluorescence increase and is linearly related to the amount of active factor $V_a$. The two isoforms of factor $V_a$, $V_{a1}$ (Frame A) and $V_{a2}$ (Frame B) were inactivated at different rates and to different extents by APC depending on the availability of C6PS.
Figure 14:
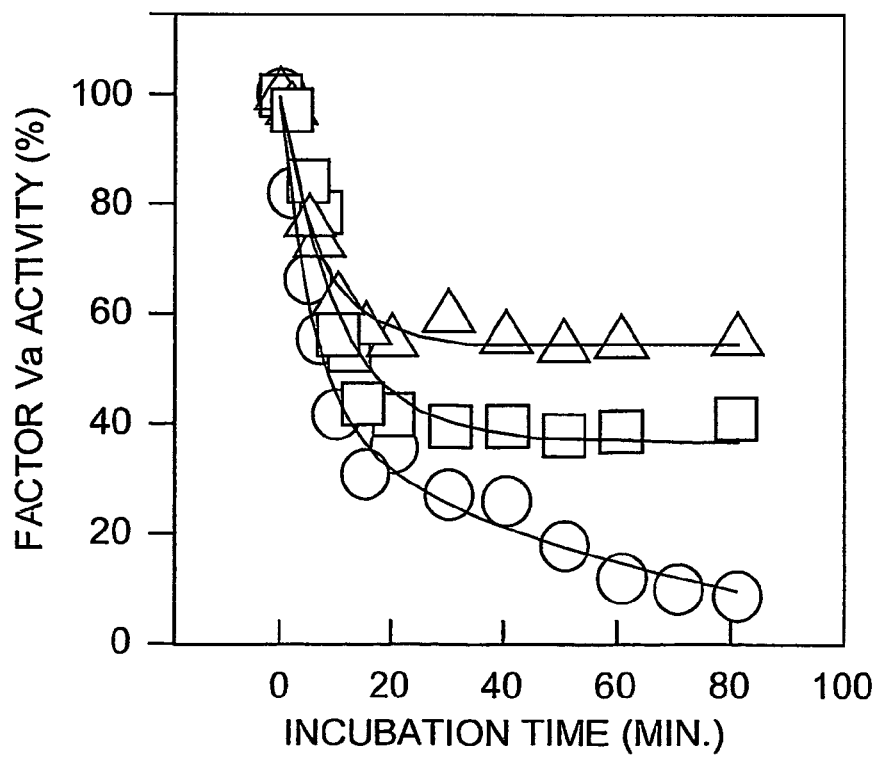

APC cuts three bonds in the heavy chain of factor $V_a$, one at $Arg^{506}$ most rapidly, one at $Arg^{306}$ less rapidly, and one at $Arg^{679}$ that probably does not affect the loss of activity of the cofactor. Proteolysis at $Arg^{506}$ leads to partial inactivation, but proteolysis at $Arg^{306}$ is necessary for full inactivation (Kalafatis & Mann (1993) J. Biol. Chemistry 268 27246; Nicolaes et al., (1995) J. Biol. Chemistry (1995) 270 21158). Membranes containing negatively charged phospholipids (especially PS) promote proteolysis of all three bonds, but the largest effect of membranes is on the proteolysis at $Arg^{306}$, a reaction that is very slow in the absence of membranes ($k_{cat}/K_M = 10^2$ to $10^3$ $M^{-1}sec^{-1}$ but increases to a rate of ($k_{cat}/K_M = 2$-$7 \times 10^6$ $M^{-1}sec^{-1}$ in the presence of PS-containing membranes (Nicolaes et al., J. Biol. Chemistry (1995) 270 21158; Hoekema et al. (1997) Biochemistry 36 3331; Egan et al. (1997) Protein Science 6 2016). We found that SPS can substitute fully for PS-containing membranes in the effect it has on proteolysis at $Arg^{306}$ (FIG. 14). The rate of proteolysis of the bond at $Arg^{306}$ increased from undetectable to a value of $k_{cat}/K_M = 3$-$3.5 \times 10^6$ $M^{-1}sec^{-1}$, identical to the rate reported with PS-containing membranes. Other experiments show that SPS binds very tightly ($k_d \sim 1$ μM) to APC, but the data in FIG. 14 show that sufficient C6PS to saturate this site (4 μM) had no effect on the rate of inactivation and only a small effect on the extent of inactivation. However, 200 μM C6PS, enough to saturate factor $V_a$ ($k_d \sim 90$ μM; Zhai et al. (2002) Biochemistry 41 5675), led to complete inactivation by promoting cleavage at $Arg^{306}$. These results indicate that PS-binding to factor $V_a$ leads to susceptibility of this bond to APC attack, and that SPS can substitute for PS-containing membranes in APC assays.

Example 4

Clotting Assays Using C6PS

Conventional lipid vesicles were compared with C6PS in two different clotting assays—the activated partial thromboplastin time (aPTT) assay and a chromogenic FVIII assay.

aPTT Assay.

Activated partial thromboplastin time assays were done using an optical detection method to determine clotting time. Two reaction mixtures were created. Mixture A had kaolin in concentrations ranging from 50 g/L to 500 g/L and either phospholipid vesicles (ranging from 0.67 to 240 μM) or C6PS (ranging from 5 μM to 5250 μM) in buffer of 20 mM HEPES (pH 7.4), 150 mM NaCl. Mixture B was 25 mM calcium chloride in a buffer of 20 mM HEPES (pH 7.4), 150 mM NaCl. Plasma, Mixture A, and Mixture B were all incubated at 37° C. for 3 minutes. Mixture A was added to plasma and incubated for 3 minutes at 37° C. Buffer B was added and the optical density was measured. Clotting was detected as an increase in absorbance.

As expected, lipid vesicles shortened the Kaolin induced clotting time in a dose-dependent fashion by as much as 100 seconds. C6PS gave a dose dependent shortening in the clotting time, but the largest decrease was 13 seconds. We speculated that the Kaolin might interfere with C6PS. Since the purpose of Kaolin is to activate the contact factors of coagulation (high molecular weight kininogen, factor XII, and factor XI), we substituted 30 nM activated factor XI for Kaolin in the assay described above. In this case, lipid vesicles were less effective, with a maximal shortening of only 80 seconds, while the C6PS was more effective with a maximal shortening of 20 seconds. This suggests that, as with assays with lipid vesicles, the composition of the activator in the aPTT can be optimized for activity with C6PS.

Chromogenic FVIII Assay.

For the chromogenic factor VII assay, a standard curve was prepared by diluting normal pooled plasma (which had 1 U/mL factor VII according to the certification sheets) into factor VII deficient plasma to give levels of 100% factor VIII, 75%, 50%, 25%, and 10% along with the factor VIII deficient plasma, which has 0% factor VIII.

Two mixtures were prepared. Mixture #1 consisted of thrombin—3 nM, factor IXa—3 nM, factor X—7.2 µg/mL, calcium—12 mM in a buffer of 20 mM Tris (pH 7.9), 150 mM NaCl. Also included in Mixture #1 were either lipid vesicles (lipid unilamellar vesicles; "LUV")—20 µM or C6PS—2, 625 µM. Mixture #2 consisted of hirudin—60 nM and Pefachrome FXa—1.8 mM in a buffer of 20 mM Tris (pH 7.9), 150 mM NaCl.

Figure 15:
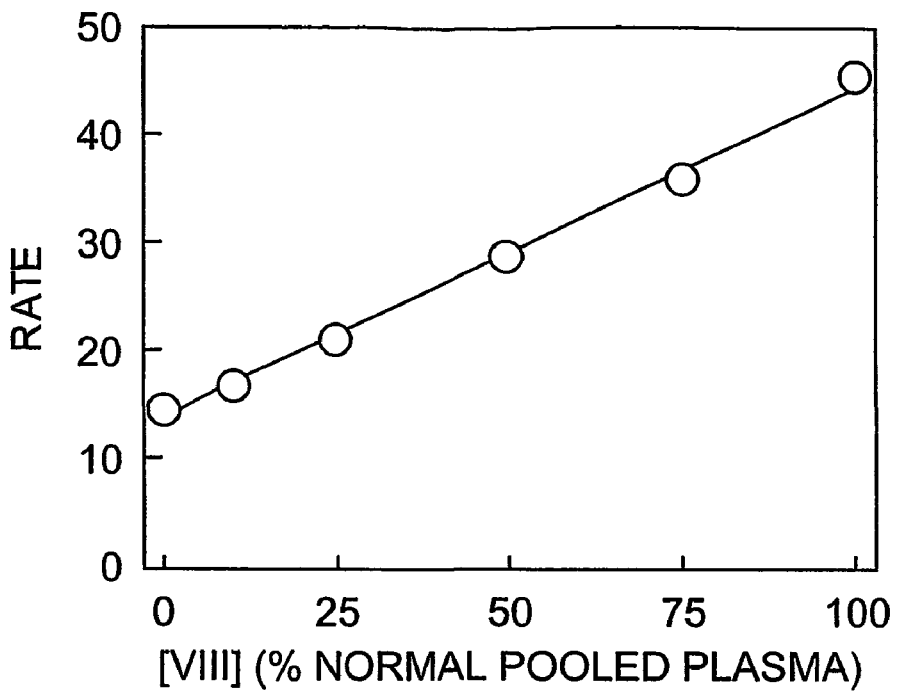
FIG. 15 shows the results of the FVIII chromogenic assay using 20 µM LUV (large unilamellar vesicles).
Figure 16:
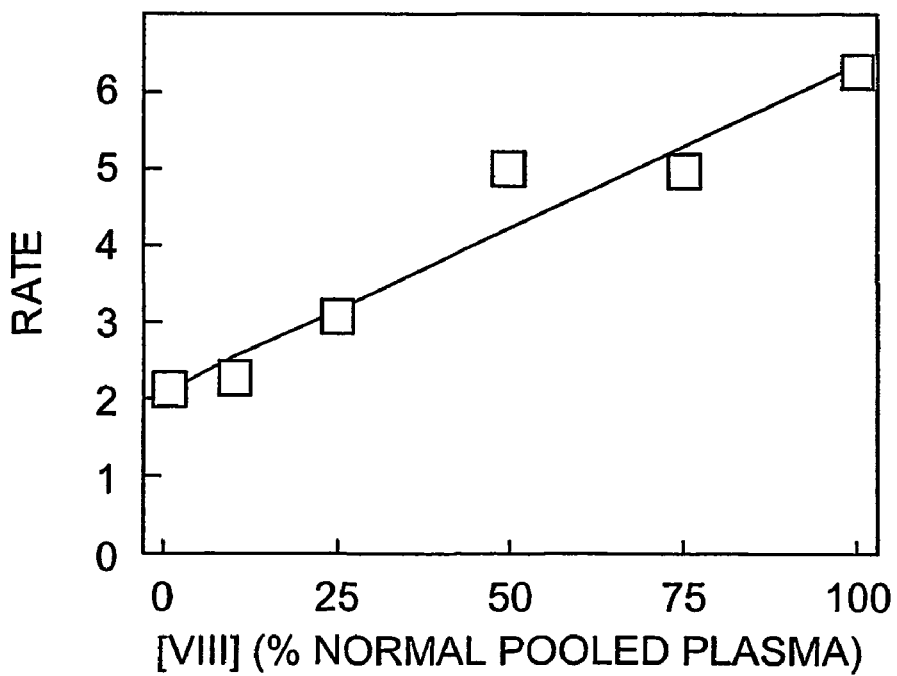
FIG. 16 shows the results of the FVIII chromogenic assay using 875 µM C6PS.

Factor VIII levels were assayed by adding 25 µL plasma to 2000 µL of buffer. 50 µL of the diluted plasma, 100 µL Mixture #1, and 100 µL of Mixture #2 were incubated at 37° C. for 3 minutes. Then 50 µL of Mixture #1 was added to diluted plasma and incubated at 37° C. for 2 minutes. Finally, 50 µL of Mixture #2 was added to diluted plasma+Mixture #1 and the reaction was monitored at 405 nm for 5 minutes. The rate is the change in absorbance between 30 seconds and 120 seconds expressed as mOD/minute. Results are shown in FIG. 15 (lipid vesicles) and FIG. 16 (C6PS).

Figure 17:
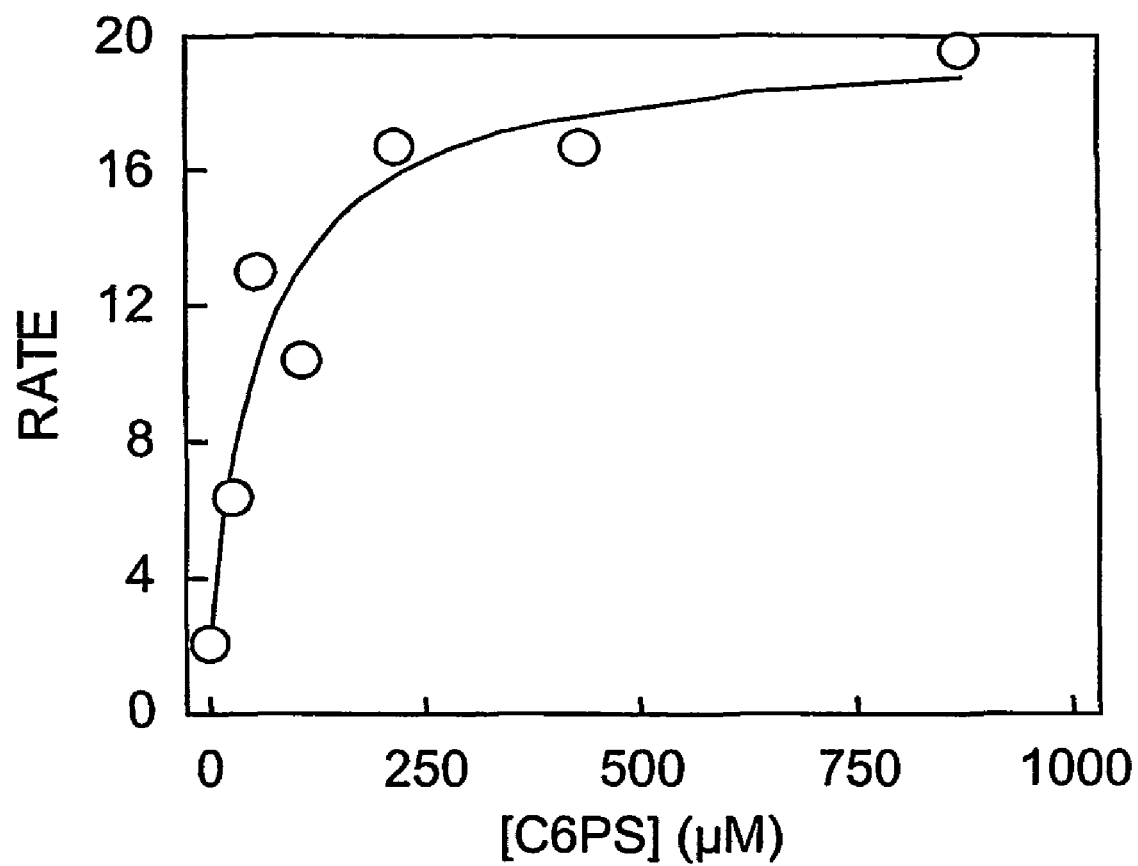
FIG. 17 illustrates the effect of varying C6PS levels on the FVIII chromogenic assay.

The effect of varying C6PS levels was also monitored as described above using normal pooled plasma (100% factor VIII), except that the concentration of C6PS in Mixture #1 was varied by serial dilution into buffer before being added to the final Mixture #1. The results are expressed as the concentration of lipid or C6PS in the final reaction mixture of 150 µM (FIG. 17) and demonstrate that the rate of clot formation saturated with C6PS concentration, yielding an appropriate concentration for the clotting assay. These results show that conditions can be found where soluble phospholipids can replace insoluble lipids in a clotting assay for factor VIII.

The foregoing examples are illustrative of the present invention, and are not to be construed as limiting thereof. The invention is described by the following claims, with equivalents of the claims to be included therein.

What is claimed is:

1. A method of evaluating clotting activity in a blood or plasma sample from a subject, the method comprising:
    (a) creating a mixture by combining in vitro the blood or plasma sample from the subject with:
        (i) a phospholipid that is soluble in the sample, wherein the phospholipid comprises phospholipids acylated by C4 to C12 fatty acids;
        (ii) a contact activator; and
        (iii) calcium;
    (b) incubating the mixture of (a) above for a time and under conditions sufficient for prothrombin activation; and
    (c) detecting Factor $X_a$ or thrombin enzyme activity, wherein the enzyme activity of Factor $X_a$ or thrombin correlates with clotting factor activity in the sample, thereby evaluating clotting activity in the sample.

2. The method of claim 1, wherein the sample is from a subject with lupus.

3. The method of claim 1, wherein the sample is further combined with Activated Protein C or a Protein C activator, wherein the level of thrombin enzyme activity correlates with Activated Protein C resistance in the sample.

4. The method of claim 3, wherein the sample is further combined with Protein S depleted plasma, wherein the level of thrombin enzyme activity inversely correlates with Protein S levels in the sample.

5. The method of claim 1, wherein the sample is further combined with a plasma selected from the group consisting of (a) plasma known to be deficient for a particular clotting factor and (b) normal plasma.

6. The method of claim 1, wherein the sample is from a subject that has been given heparin treatment.

7. The method of any of claims 1-6, wherein thrombin enzymatic activity is measured.

8. The method of any of claims 1-6, wherein clot formation is detected.

9. The method of claim 1, wherein the phospholipid consists essentially of a phospholipid selected from the group consisting of phosphatidylserine, phosphatidylhomoserine, phosphatidic acid, phosphatidylethanolamine, and a combination thereof.

10. The method of claim 9, wherein the phospholipid consists essentially of phosphatidylserine acylated by C4 to C12 fatty acids.

11. The method of claim 1, wherein the phospholipid is added to a final concentration from about 4 µM to about 2 mM.

12. The method of claim 1, wherein the phospholipid is in a dried form prior to combination with the sample.

13. The method of claim 1, wherein the sample is a human blood or plasma sample.

14. The method of claim 1, further comprising comparing the detected thrombin enzymatic activity with a standard.

15. The method of claim 1, wherein the contact activator is selected from the group consisting of kaolin, clay, silica, ellagic acid, celite, diatomaceous earth, glass beads, and a combination thereof.

16. A method of evaluating clotting activity in a blood or plasma sample from a subject, the method comprising:
    (a) creating a mixture by combining in vitro the blood or plasma sample from the subject with:
        (i) a phospholipid that is soluble in the sample to a final concentration of 50 µM to 2 mM phospholipid, wherein the phospholipid comprises phospholipids acylated by C4 to C12 fatty acids;
        (ii) a contact activator; and
        (iii) calcium;
    (b) incubating the mixture of (a) above for a time and under conditions sufficient for prothrombin activation; and
    (c) detecting Factor $X_a$ or thrombin enzyme activity, wherein the enzyme activity of Factor $X_a$ or thrombin correlates with clotting factor activity in the sample, thereby evaluating clotting activity in the sample.

17. The method of claim 16, wherein the phospholipid is added to a final concentration of 100 µM to 2 mM.

18. The method of claim 16, wherein the phospholipid consists essentially of phospholipids acylated by C4 to C12 fatty acids.

19. The method of claim 16, wherein the sample is from a subject with lupus.

20. A method of evaluating clotting activity in a blood or plasma sample from a subject, the method comprising:
(a) creating a mixture by combining in vitro the blood or plasma sample from the subject with:
(i) a phospholipid that is soluble in the sample and contains no detectable aggregates as determined by quasi-electric light scattering techniques, wherein the phospholipid comprises phospholipids acylated by C4 to C12 fatty acids;
(ii) a contact activator; and
(iii) calcium;
(b) incubating the mixture of (a) above for a time and under conditions sufficient for prothrombin activation; and
(c) detecting Factor $X_a$ or thrombin enzyme activity, wherein the enzyme activity of Factor $X_a$ or thrombin correlates with clotting factor activity in the sample, thereby evaluating clotting activity in the sample.

21. The method of claim 20, wherein the phospholipid is added to a final concentration of 50 μM to 2 mM.

22. The method of claim 20, wherein the phospholipid is added to a final concentration of 100 μM to 2 mM.

23. The method of claim 20, wherein the phospholipid consists essentially of phospholipids acylated by C4 to C12 fatty acids.

24. The method of claim 20, wherein the sample is from a subject with lupus.

25. A method of evaluating clotting activity in a blood or plasma sample from a subject, the method comprising:
(a) creating a mixture by combining in vitro the blood or plasma sample from the subject with:
(i) a phospholipid that is soluble in the sample and consists essentially of phospholipids acylated by C4 to C12 fatty acids;
(ii) a contact activator; and
(iii) calcium;
(b) incubating the mixture of (a) above for a time and under conditions sufficient for prothrombin activation; and
(c) detecting Factor $X_a$ or thrombin enzyme activity, wherein the enzyme activity of Factor $X_a$ or thrombin correlates with clotting factor activity in the sample, thereby evaluating clotting activity in the sample.

26. The method of claim 25, wherein the phospholipid is added to a final concentration of 50 μM to 2 mM.

27. The method of claim 25, wherein the phospholipid is added to a final concentration of 100 μM to 2 mM.

28. The method of claim 25, wherein the phospholipid consists essentially of phospholipids acylated by C4 to C10 fatty acids.

29. The method of claim 25, wherein the sample is from a subject with lupus.

30. The method of claim 1, wherein the phospholipid consists essentially of phospholipids acylated by C4 to C12 fatty acids.

* * * * *

UNITED STATES PATENT AND TRADEMARK OFFICE
CERTIFICATE OF CORRECTION

PATENT NO. : 7,727,736 B2  Page 1 of 1
APPLICATION NO. : 10/572521
DATED : June 1, 2010
INVENTOR(S) : Lentz et al.

It is certified that error appears in the above-identified patent and that said Letters Patent is hereby corrected as shown below:

In the Specification

Column 1, lines 6-9, Related Application Information: Please replace the entire paragraph with the following:

-- This application is a 35 U.S.C. §371 national phase application of International Application Serial No. PCT/US2004/030987, filed on September 21, 2004 which claims the benefit of U.S. Provisional Application No. 60/504,796, filed September 22, 2003, the disclosures of which are incorporated herein by reference in their entireties. --

Signed and Sealed this

Thirtieth Day of November, 2010

David J. Kappos
*Director of the United States Patent and Trademark Office*